United States Patent
Lauerman

(10) Patent No.: US 9,289,513 B2
(45) Date of Patent: Mar. 22, 2016

(54) TARGETED CYTOKINE FOR TREATMENT OF MUSCULOSKELETAL DISEASES

(75) Inventor: Tod Lauerman, San Diego, CA (US)

(73) Assignee: OPTION PHARMACEUTICALS, LLC, Vista, CA (US)

(*) Notice: Subject to any disclaimer, the term of this patent is extended or adjusted under 35 U.S.C. 154(b) by 0 days.

(21) Appl. No.: 14/006,944

(22) PCT Filed: Mar. 21, 2012

(86) PCT No.: PCT/US2012/029983
§ 371 (c)(1),
(2), (4) Date: Dec. 2, 2013

(87) PCT Pub. No.: WO2012/129330
PCT Pub. Date: Sep. 27, 2012

(65) Prior Publication Data
US 2014/0170171 A1 Jun. 19, 2014

Related U.S. Application Data

(60) Provisional application No. 61/466,877, filed on Mar. 23, 2011.

(51) Int. Cl.
*A61K 38/18* (2006.01)
*A61K 47/42* (2006.01)
*A61K 47/48* (2006.01)
*C07K 14/495* (2006.01)

(52) U.S. Cl.
CPC ....... *A61K 47/48415* (2013.01); *A61K 38/1841* (2013.01); *C07K 14/495* (2013.01); *C07K 2319/30* (2013.01)

(58) Field of Classification Search
None
See application file for complete search history.

(56) References Cited

U.S. PATENT DOCUMENTS

| | | | |
|---|---|---|---|
| 5,998,598 | A | 12/1999 | Csaky et al. |
| 2003/0166163 | A1 | 9/2003 | Gillies |
| 2005/0276802 | A1 | 12/2005 | Adams et al. |
| 2006/0275211 | A1 | 12/2006 | Jakobovits et al. |
| 2008/0050375 | A1 | 2/2008 | Davies et al. |
| 2008/0286819 | A1 | 11/2008 | Ravetch et al. |

FOREIGN PATENT DOCUMENTS

| | | |
|---|---|---|
| CN | 1435433 | 8/2003 |
| WO | WO-97/43316 | 11/1997 |
| WO | WO-98/40498 | 9/1998 |
| WO | WO-2006/116002 | 11/2006 |
| WO | WO-2010/077831 | 7/2010 |

OTHER PUBLICATIONS

Rowley et al. B lymphocytes secreting IgG linked to latent transforming growth factor-beta prevent primary cytolytic T lymphocyte responses. Int Immunol. Mar. 1998;10(3):355-63.*
Massagué J. The TGF-beta family of growth and differentiation factors. Cell. May 22, 1987;49(4):437-8.*
Musculoskeletal Diseases, in MeSH Database, NCBI, Bethesda, Maryland, USA [online], [retrieved on Feb. 18, 2015]. Retrieved from the Internet: <URL: http://www.ncbi.nlm.nih.gov/mesh/?term=musculoskeletal+disease>.*
Shen et al. Bone morphogenetic proteins regulate ionotropic glutamate receptors in human retina. Eur J Neurosci. Oct. 2004;20(8):2031-7.*
Umlauf et al. Cartilage biology, pathology, and repair. Cell Mol Life Sci. Dec. 2010;67(24):4197-211. Epub Aug. 25, 2010.*
Vukicevic et al. Induction of nephrogenic mesenchyme by osteogenic protein 1 (bone morphogenetic protein 7). Proc Natl Acad Sci U S A. Aug. 20, 1996;93(17):9021-6.*
Adams et al., "Transforming growth factor-beta induces human T lymphocyte migration in vitro," Journal of Immunology (1991) 147:609-612.
Armour et al., "Differential binding to human FcgammaRIIa and FcgammaRIIb receptors by human IgG wildtype and mutant antibodies," Mol. Immunol. (2003) 40:585-593.
Bouchard et al., "A transforming growth factor beta-like immunosuppressive factor in immunoglobulin G-binding factor," J. Exp. Med. (1995) 182:1717-1726.
Bruhns et al., "Specificity and affinity of human Fcgamma receptors and their polymorphic variants for human IgG subclasses," Blood (2009) 113(16):3716-3725.
Calabresi et al., "Phase 1 trial of transforming growth factor beta 2 in chronic progressive MS," Neurology (1998) 51:289-292.
Caver et al., "Intracellular demonstration of active TGFbeta1 in B cells and plasma cells of autoimmune mice. IgG-bound TGFbeta1 suppresses neutrophil function and host defense against Staphylococcus aureus infection," Journal of Clinical Investigation (1996) 98(11):2496-2506.
Curiel et al., "Adenovirus enhancement of transferrin-polylysine-mediated gene delivery," PNAS USA (1991) 88:8850-8854.
Gordon et al., "Monocyte and macrophage heterogeneity," Nat. Rev. Immunol. (2005) 5(12):953-964.
Gordon, "Alternative activation of macrophages," Nat. Rev. Immunol. (2003) 3:23-35.
Harada et al., "Circulating immunoglobulin-bound transforming growth factor beta at a late tumour-bearing stage impairs antigen-specific responses of CD4+ T cells," Clin. Exp. Immunol. (2002) 128:204-212.
Highton et al., "Changes in the phenotype of monocytes/macrophages and expression of cytokine mRNA in peripheral blood and synovial fluid of patients with rheumatoid arthritis," Clin. Exp. Immunol. (1995) 102:541-546.

(Continued)

*Primary Examiner* — David Romeo
(74) *Attorney, Agent, or Firm* — Morrsion & Foerster LLP

(57) ABSTRACT

Provided are proteins and polynucleotides, complexes and compositions containing the proteins, and methods for their use in administration to subjects and for disease treatment. Among the provided proteins and complexes are complexes containing a TGF-beta associated with immunoglobulins (such as IgGs) or functional portions thereof including Fc portions, such as by non-covalent bonds. The complexes and compositions can be used for administration to subjects, such as for treating a subject with a musculoskeletal disease such as osteoarthritis and/or degenerative joint disease. The complexes and compositions can be used in different mammals, including dogs, horses, and humans.

8 Claims, No Drawings

(56) References Cited

OTHER PUBLICATIONS

International Preliminary Report on Patentability for PCT/US09/67945, issued Jun. 21, 2011, 10 pages.
International Preliminary Report on Patentability for PCT/US2012/029983, issued Sep. 24, 2013, 7 pages.
International Search Report for PCT/US09/67945, mailed Mar. 9, 2010, 3 pages.
International Search Report and Written Opinion for PCT/US2012/029983, mailed Jul. 2, 2012, 11 pages.
Kaveri et al., "The anti-inflammatory IgG," New England Journal of Medicine (2008) 359(3):307-309.
Lewis and Pollard, "Distinct role of macrophages in different tumor microenvironments," Cancer Res. (2006) 66:605-612.
Maenaka et al., "The human low affinity Fcgamma receptors IIa, IIb, and III bind IgG with fast kinetics and distinct thermodynamic properties," J. Biol. Chem. (2001) 276(48):44898-44904.
Massague, "The TGF-beta family of growth and differentiation factors," Cell (1987) 49:437-438.
Nimmerjahn and Ravetch, "Divergent immunoglobulin g subclass activity through selective Fc receptor binding," Science (2005) 310:1510-1512.
Nimmerjahn et al., "FcgammaRIV: a novel FcR with distinct IgG subclass specificity," Immunity (2005) 23:41-51.
Parekh et al., "Neutrophil Chemotaxis in Response to TGF-$\beta$ Isoforms (TGF-$\beta$1, TGF-$\beta$2, TGF-$\beta$3) Is Mediated by Fibronectin," Journal of Immunology (1994) 152:2456-2466.
Perkett et al., "Transforming growth factor-beta activity in sheep lung lymph during the development of pulmonary hypertension," J. Clin. Invest. (1990) 86:1459-1464.
Richards et al., "Optimization of antibody binding to FcgammaRIIa enhances macrophage phagocytosis of tumor cells," Mol. Cancer Ther. (2008) 7(8):2517-2527.
Rowley et al., "B lymphocytes secreting IgG linked to latent transforming growth factor-beta prevent primary cytolytic T lymphocyte responses," Int. Immunol. (1998) 10(3):355-363.
Seitz et al., "Effects of methotrexate on differentiation of monocytes and production of cytokine inhibitors by monocytes," Arthritis & Rheumatism (1998) 41(11):2032-2038.
Shen et al., "Bone morphogenetic proteins regulate ionotropic glutamate receptors in human retina," Eur. J. Neurosci. (2004) 20:2031-2037.
Sica et al., "Tumour-associated macrophages are a distinct M2 polarised population promoting tumour progression: potential targets of anti-cancer therapy," European Journal of Cancer (2006) 42:717-727.
Stach and Rowley, "A first or dominant immunization. II. Induced immunoglobulin carries transforming growth factor beta and suppresses cytolytic T cell responses to unrelated alloantigens," J. Exp. Med. (1993) 178:841-852.

Terrell et al., "Pathology of Recombinant Human Transforming Growth Factor-$\beta$1 in Rats and Rabbits" in International Review of Experimental Pathology, vol. 1 (1993) pp. 43-67.
Van Der Kraan et al., "TGF-beta signaling in chondrocyte terminal differentiation and osteoarthritis: modulation and integration of signaling pathways through receptor-Smads," Osteoarthritis Cartilage (2009) 17(12):1539-1545.
Vukicevic et al., "Induction of nephrogenic mesenchyme by osteogenic protein 1 (bone morphogenetic protein 7)," PNAS USA (1996) 93:9021-9026.
Wahl et al., "Transforming growth factor type beta induces monocyte chemotaxis and growth factor production," PNAS USA (1987) 84:5788-5792.
Wakefield et al., "Recombinant latent transforming growth factor beta 1 has a longer plasma half-life in rats than active transforming growth factor beta 1, and a different tissue distribution," Journal of Clinical Investigation (1990) 86:1976-1984.
Zitterkopf et al., "Hydrophobic IgG-containing immune complexes in the plasma of autoimmune MRL/lpr mice, lactate dehydrogenase-elevating virus-infected mice, and pigs: association with transforming growth factor-beta and pH-dependent amplification," Viral Immunology (2003) 16(4):511-523.
Restriction Requirement for U.S. Appl. No. 13/140,350, mailed Sep. 11, 2012, 10 pages.
Response to Restriction Requirement for U.S. Appl. No. 13/140,350, filed Oct. 11, 2012, 6 pages.
Office Action for U.S. Appl. No. 13/140,350, mailed Dec. 10, 2012, 12 pages.
Response to Office Action for U.S. Appl. No. 13/140,350, filed Apr. 8, 2013, 19 pages.
Final Office Action for U.S. Appl. No. 13/140,350, mailed Jun. 13, 2013, 13 pages.
Response to Final Office Action for U.S. Appl. No. 13/140,350, filed Sep. 13, 2013, 13 pages.
Advisory Action for U.S. Appl. No. 13/140,350, mailed Sep. 24, 2013, 3 pages.
Supplemental Response to Final Office Action for U.S. Appl. No. 13/140,350, filed Oct. 18, 2013, 9 pages.
Notice of Allowance for U.S. Appl. No. 13/140,350, mailed Nov. 12, 2013, 10 pages.
Communication pursuant to Rules 161(1) and 162 EPC for EP 12711326.4, mailed Nov. 4, 2013, 2 pages.
Response to Communication pursuant to Rules 161(1) and 162 EPC for EP 12711326.4, filed May 14, 2014, 17 pages.
Communication pursuant to Article 94(3) EPC for EP 12 711 326.4, mailed Jul. 27, 2015, 6 pages.

* cited by examiner

TARGETED CYTOKINE FOR TREATMENT OF MUSCULOSKELETAL DISEASES

RELATED APPLICATIONS

This application is a U.S. National Phase Application of International Application No. PCT/US2012/029983, filed Mar. 21, 2012, which claims priority to U.S. Provisional Patent Application Ser. No. 61/466,877, filed on Mar. 23, 2011, the contents of which are incorporated by reference herein.

REFERENCE TO SEQUENCE LISTING SUBMITTED VIA EFS-WEB

The entire content of the following electronic submission of the sequence listing via the USPTO EFS-WEB server, as authorized and set forth in MPEP §1730 II.B.2(a)(C), is incorporated herein by reference in its entirety for all purposes. The sequence listing is identified on the electronically filed text file as follows:

| File Name | Date of Creation | Size (bytes) |
| --- | --- | --- |
| 655162000440Seqlist | Mar. 19, 2012 | 8,856 bytes |

TECHNICAL FIELD

Provided are proteins, such as transforming growth factor-beta (TGF-beta) proteins, including targeted TGF-beta proteins, and immunoglobulin (Ig) proteins, and complexes of the proteins, such as TGF-beta-Ig complexes, including TGF-beta IgG complexes; compositions and combinations containing the proteins and complexes; processes for making such proteins and complexes; and methods for disease treatment, such as methods for treatment of osteoarthritis, by administering such proteins, complexes, combinations, and compositions.

BACKGROUND

TGF-beta belongs to a superfamily of structurally related regulatory proteins, which includes activin/inhibin and bone morphogenic proteins. Three isoforms of TGF-beta are produced in mammals: TGF-beta 1, TGF-beta 2, and TGF-beta 3. TGF-beta forms a homodimer, which typically is secreted as an inactive, latent complex, having two covalently linked propeptides (the latency-associated protein, or "LAP"), non-covalently bound to, and inactivating, the dimeric mature TGF-beta molecule. Activation of the latent complex in vivo occurs either through dissociation of the TGF-beta dimer from LAP (via proteases, nitric oxide, or other means), or through a conformational change in the latent complex caused by binding of LAP to either thrombospondin or αvβ6 integrin. Active TGF-beta dimers specifically bind to TGF-beta Receptor II (TGF-beta RII), and typically bind two TGF-beta RII molecules. Binding by the TGF-beta homodimer recruits two TGF-beta Receptor I (TGF-beta RI) molecules, forming a heteromeric complex. Downstream signaling is mediated by the bound TGF-beta RI, a serine-threonine kinase, which is phosphorylated upon complexation to the TGF-beta/TGF-beta RII complex. Activation of TGF-beta RI causes phosphorylation of Smad2 and Smad3 and induces their heterodimerization with Smad4. The activated Smad complex then translocates to the nucleus where it regulates gene transcription.

TGF-beta regulates a plurality of processes, including cell differentiation and proliferation, migration, motility, deposition of the extracellular matrix, cell death, and immunosuppression. TGF-beta signaling can increase the synthesis of matrix proteins, such as vitronectin, fibronectin, laminin, tenascin, proteoglycans, and collagens, enhance the expression of cell adhesion molecules such as integrins, and increase the synthesis of various protease inhibitors. It also can decrease the synthesis of matrix degrading proteases.

TGF-beta is a potent anabolic factor in cartilage growth and retention. TGF-beta is found in many tissues, including bone matrix, cartilage, platelets, lymphocytes and other tissues (R. D. Coutts, R. L. Sah & D. Amiel: Instructional Course Lect 47, 487-94, American Academy Orthopaedic Surgery, Rosemont, Ill., (1997)). TGF-beta is a more potent stimulator of chondrocyte proliferation than other cytokines that have been described to have this activity (P. Guerne, A. Sublet & M. Lotz, *J Cell Physiol* 158: 476-84 (1994)). TGF-beta also has the ability to down-regulate cytokines that have a catabolic activity towards chondrocytes (H. Van Beuningen, P. Van der Kraan, O. Arntz & W. Van den Berg, *Ann Rheum Dis* 52, 185-91 (1993)).

Fc receptors are cell surface receptors, expressed on various immune cell types that specifically bind Fc regions of immunoglobulin molecules. The Fc region is an effector-function conferring portion of the immunoglobulin constant region. Fc receptors are generally categorized according to the class of Ig molecule they recognize. For example, Fc gamma receptors (FcγR) bind Fc portions of IgG molecules. Mammalian Fc gamma receptors are further classified into four classes (FcγRI (CD64), FcγRII (CD32), FcγRIII (CD16) and FcγRIV). The FcγRII class further includes the functionally distinct FcγRIIa and FcγRIIb sub-types. FcγRI has a high affinity for IgG Fc regions, can bind monomeric IgG at physiological concentrations of IgG, and has a restricted isotype specificity. FcγII and FcγIII receptors have low affinities for IgG Fc regions and typically only can bind multimeric IgG (for example, immune complexes and dimeric IgG) at physiological IgG concentrations.

Human osteoarthritis is the most common form of arthritis and is the most common musculoskeletal disease in the developed world. Osteoarthritis is characterized by cartilage damage, synovial fibrosis, sclerosis of the subchondral bone and osteophyte formation. Clinically, osteoarthritis involves chronic pain, tenderness and a reduced range of motion in the affected joint. Cartilage damage is an extremely important clinical manifestation of the disease. Cartilage has a limited intrinsic ability of repair and renewal, thus cartilage damage leads to progressive disease.

Osteoarthritis is a disease which is contained within the synovial lining of the affected joint. The synovial lining is composed of two cell types: type A, which is a macrophage-like cell that is capable of phagocytosis and possesses functional FcγR (Perez-Maceda, B, *Rev Esp Fisiol.* 42(3):301-8 (1986).) and type B, which is a fibroblast-type cell.

In osteoarthritic joints, several catabolic and pain mediators are present at high concentration relative to non-arthritic joints, and may be responsible for clinical pathology of the disease (Loeser, R F et al., *Arthritis & Rheumatism,* 46:2349-2357 (2002) and references therein). Interleukin-1beta (IL-1b) is a primary catabolic factor in joints which inhibits chondrocyte differentiation and cartilage growth and retention, and has been shown have an increased concentration in arthritic joints. IL-1b has also been shown to increase the expression of the enzyme inducible nitric oxide synthetase (iNOS) in chondrocytes, an enzyme that produces the chemical messenger nitric oxide. Nitric oxide (NO), which has also been shown to be present at high concentrations in arthritic joints, also causes inhibition of chondrocyte differentiation and cartilage growth and retention. Both IL-1b and nitric oxide have been shown to be pain receptor agonists (Cunha, T M et al., *PNAS* 102:1755-1760 (2005) and Binshtok, A M et al., *J. Neuroscience* 28(52):14062-14073 (2008)).

Osteoarthritis is also a common disease in companion animals. For example, in dogs osteoarthritis (also known as degenerative joint disease) has been estimated to affect up to 20% of all companion dogs in the US over one year of age. A survey of working military dogs found that osteoarthritis was the number one cause of death or reason for euthanizing this group of dogs. Osteoarthritis is also common in cats and horses, and can be lethal in the latter species.

Available treatments for osteoarthritis are limited. For example, osteoarthritis of the knee, the most common form of human osteoarthritis, is usually treated pharmacologically, including analgesics and non-steroidal anti-inflammatory drugs (NSAIDs). Non-pharmacological treatments include patient education, weight loss and exercise. Invasive treatments include steroid injections, hyaluronic acid injections and surgery, including joint replacement surgery.

New therapeutics with increased efficacy (both with respect to pain reduction and amelioration of cartilage destruction), half-life and specificity are needed. As an anabolic factor for cartilage growth and chondrocyte differentiation, TGF-beta is an attractive candidate for producing therapeutic effects in osteoarthritis. However, available TGF-beta proteins and their use in treating diseases are limited. In particular, there is a need for TGF-beta proteins and complexes, including targeted TGF-beta proteins and complexes, with improved in vivo half-lives, and for TGF-beta proteins and complexes having specificity for particular cell types and specific effects on particular cell types within the synovium. Accordingly, it is among the objects of the invention to provide TGF-beta proteins, complexes (e.g. multimers, such as dimers), including proteins and complexes with high efficacy, specificity, availability and half-life, and combinations and compositions containing the TGF-beta proteins, and methods for treating diseases with the proteins and complexes.

SUMMARY

Provided herein are TGF-beta proteins and complexes (e.g. multimers, dimers) containing the TGF-beta proteins, such as complexes containing TGF-beta proteins and immunoglobulins or portions thereof. The TGF-beta complexes can be targeted to particular cell types based on their affinities for receptors differentially expressed on different cells, such as macrophages. The provided proteins and complexes include those with long in vivo half-lives, those with specificity to particular cell types, and those having no pleiotropic effects, or having reduced pleiotropic effects compared to free TGF-beta proteins. The provided proteins and complexes can be used to treat diseases such as musculoskeletal diseases. For example, in one embodiment, the provided proteins and complexes can be used in treatment of diseases such as osteoarthritis and degenerative joint disease. Uses and methods of using the provided proteins and complexes for administration to subjects and treating diseases also are provided. Also provided are combinations and compositions, e.g. pharmaceutical compositions, containing the TGF-beta proteins and complexes, and methods for using the provided compositions.

Among the provided complexes are Transforming Growth Factor-beta-bound IgGs (TIGGs). The TIGG is typically an isolated or purified TIGG. Typically, the provided complex (e.g. the TIGG) contains an immunoglobulin (Ig) portion and a transforming growth factor-beta (TGF-beta) portion, which contain one or more Ig protein and one or more TGF-beta protein, respectively.

The Ig portion can contain one Ig protein, or a plurality of Ig proteins, which can be full length Ig molecules or functional regions thereof, and include wild-type and variant Ig proteins as described herein. The Ig protein can be any known Ig protein, including a full-length immunoglobulin (such as a human IgG or another mammalian form of IgG) or functional region thereof such as an Fc region or portion thereof, including the Ig proteins disclosed herein. Typically, the Ig protein is an IgG (in the case of a TIGG) or functional region thereof. The Ig proteins include proteins with an Fc region having at least at or about 80% sequence identity to the sequence of amino acids set forth in SEQ ID NO:2, SEQ ID NO:3, SEQ ID NO:4 or SEQ ID NO:5. In one aspect, the Ig protein is a portion of an Ig molecule, such as an Fc region having at least at or about 70%, at least at or about 75%, or at least at or about 80%, such as at least at or about or at or about 80, 81, 82, 83, 84, 85, 86, 87, 88, 89, 90, 91, 92, 93, 94, 95, 96, 97, 98, 99 or 100% sequence identity to the sequence of amino acids set forth in SEQ ID NO:2, SEQ ID NO:3, SEQ ID NO:4 or SEQ ID NO:5.

The TGF-beta portion contains one or more TGF-beta protein. In one example, the TGF-beta portion contains two TGF-beta proteins that are monomers associated to form a dimer via covalent bond, such as an activated, mature, TGF-beta homodimer, for example, a 25 kDa TGF-beta homodimer or variant thereof. The TGF-beta protein can be any known TGF-beta, including TGF-beta 1, TGF-beta 2 and TGF-beta 3 and monomers thereof, and any of the TGF-beta proteins described herein, including variants that retain TGF-beta activity. In one embodiment, the TGF-beta protein has at least at or about 70%, at least at or about 75%, or at least at or about 80%, such as at least at or about or at or about 80, 81, 82, 83, 84, 85, 86, 87, 88, 89, 90, 91, 92, 93, 94, 95, 96, 97, 98, 99 or 100%, sequence identity to the sequence of amino acids set forth in SEQ ID NO:1.

The Ig portion and the TGF-beta portion of the complex (e.g. the TIGG) (e.g. the Ig protein(s) and the TGF-beta protein(s) thereof) are associated, typically by a non-covalent bond. In one example, the complex contains two Ig proteins associated with two TGF-beta proteins, such as the monomers of a TGF-beta dimer (homodimer or heterodimer). Typically, the Ig protein(s) and the TGF-beta protein(s) are associated directly, without an intermediate protein or peptide. For example, in one aspect, the complex (e.g. TIGG) does not contain a latent-associated protein. In one example, the complex contains a TGF-beta dimer where each monomer subunit of the TGF-beta dimer is non-covalently bound to an Ig protein of the Ig portion.

In another example, the Ig protein contains an Fc region having at least 80% sequence identity to the sequence of amino acids set forth in any of SEQ ID NOs: 2, 3, 4 and 5, or is an Fc region having at least 80% sequence identity to the sequence of amino acids set forth in any of SEQ ID NOs: 2, 3, 4 and 5.

The complexes further typically have TGF-beta activity. In one embodiment, the TIGG has TGF-beta activity at a physiological pH after having been activated. Activation of the TIGG complex can occur chemically, for example, by low pH treatment for several minutes, or by cellular means, for example, interaction with macrophages or other cells which possess functional FcγR In another embodiment, the TGF-beta activity is at least substantially the same as the TGF-beta activity of a wild-type TGF-beta or other TGF-beta described herein, such as the TGF-beta activity of a TGF-beta protein having the amino acid sequence set forth in SEQ ID NO: 1.

Also provided are mixtures of the TGF-beta containing complexes. The mixtures can include Ig portions of different isotypes and/or sub-types (including different variant Ig proteins). In one example, the mixture contains a plurality of TIGGs, where the various Ig portions contain Immunoglobulins of a human gamma globulin, or IVIG mixture. The mixtures include mixtures of any of the provided complexes, in any desired combination.

Also provided are vectors encoding the complexes, such as vectors encoding the any of the TIGGs. For example, in one embodiment, the vector contains a polynucleotide encoding a TGF-beta protein having at least at or about 80% sequence identity to the sequence of amino acids set forth in SEQ ID NO:1, and a polynucleotide encoding an Ig protein containing an Fc region having at least at or about 80% sequence identity to an amino acid sequence set forth in any of SEQ ID NO:2, SEQ ID NO:3, SEQ ID NO:4 and SEQ ID NO:5. The vectors include viral vectors.

Also provided are host cells containing the vectors, and processes for producing the complexes, such as the TIGG complexes, using the vectors. In one embodiment, the process is performed by culturing the host cell under conditions sufficient for the production of proteins encoded by the polynucleotides, and recovering the TIGG, the TGF-beta protein, and/or the Ig protein. Also provided are processes for producing the complexes including the TIGGs. In one embodiment, the process is performed by combining a TGF-beta protein and an Ig protein under conditions whereby they associate via a non-covalent bond and separating the TIGG from free TGF-beta and free Ig, thereby recovering the TIGG. In one aspect, the TGF-beta protein and Ig protein are incubated in a buffer having a pH of at least at or about 7, at or about 8, at or about 9, at or about 10, or at or about 11.

Also provided are pharmaceutical compositions containing the complexes, such as any of the TIGG complexes, and/or the mixtures, admixed with a pharmaceutically acceptable carrier.

The TIGGs, mixtures and compositions can be administered to a subject to treat, ameliorate, and/or prevent diseases and conditions and symptoms thereof. Provided are methods for administering the compositions, complexes (TIGGs) and mixtures to subjects to treat, ameliorate or prevent such diseases and uses of the compositions, mixtures and complexes in such therapies and in preparing medicaments for treating, ameliorating and/or preventing such diseases and conditions.

Among the diseases treated by the methods, uses and pharmaceutical compositions are those associated with musculoskeletal diseases such as osteoarthritis and degenerative joint disease.

For example, provided are methods for treating a subject having a musculoskeletal disease by administering a therapeutically effective amount of the pharmaceutical composition to the subject.

Also provided are methods for reducing pain in a subject, comprising administering a therapeutically effective amount of the pharmaceutical composition to the subject, and uses of the provided compositions and complexes in reducing pain.

Also provided are methods for reducing cartilage damage, reducing or halting the progress of cartilage damage, or reversing cartilage damage in a subject with a musculoskeletal disease or condition. In one embodiment, the disease or condition is osteoarthritis. In another embodiment, the disease is a degenerative joint disease.

Also provided are methods for preventing or reducing the chances of osteoarthritis recurrence in a subject following surgery for osteoarthritis or in a subject that has sustained muscle, ligament, cartilage or other structural damage to a joint by administering a therapeutically effective amount of the pharmaceutical composition to the subject.

The pharmaceutical compositions can be administered by any route, such as subcutaneously, transdermally, orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, or intrathecally. In one embodiment, the pharmaceutical composition is administered by intra-articular injection. In another embodiment, the pharmaceutical composition is administered by intra-articular injection after arthrocentesis. In another embodiment, the administration is intravenous, subcutaneous or subdermal injection.

DETAILED DESCRIPTION

Outline
A. Definitions
B. TGF-beta proteins, complexes containing TGF-beta proteins, and methods of use
   i. TGF-beta
   ii. Immunoglobulins and Fc Receptors
   iii. Complexes, including TGF-beta—IgGs (TIGGs)
      a. Naturally occurring and purified TGF-beta—IgG complexes
      b. TGF-beta portions of the provided complexes
      c. Immunoglobulin portions of the complexes
      d. Association of the TGF-beta and Ig portions of the complex
   vi. Polynucleotides
   vii. Methods of producing the TIGG complexes
   viii. Methods for evaluating the TGF-beta containing complexes
      a. Binding affinities
      b. Activity
C. Therapeutic Applications
   i. Methods of using TIGGs
D. Pharmaceutical Compositions, dosing and administration
E. EXAMPLES A. Definitions Unless defined otherwise, all technical and scientific terms used herein have the same meaning as is commonly understood by one of ordinary skill in the art to which this invention belongs. All patents, published patent applications, other publications and sequences from GenBank, and other databases referred to herein are incorporated by reference in their entirety. If a definition set forth in this section is contrary to, or otherwise inconsistent with, a definition set forth in patents, published patent applications and other publications and sequences from GenBank and other data bases that are herein incorporated by reference, the definition set forth in this section prevails over the definition that is incorporated herein by reference.

The practice of the provided embodiments will employ, unless otherwise indicated, conventional techniques of molecular biology and the like, which are within the skill of the art. Such techniques are explained fully in the literature.

See e.g., Molecular Cloning: A Laboratory Manual, (J. Sambrook et al., Cold Spring Harbor Laboratory, Cold Spring Harbor, N.Y., 1989); Current Protocols in Molecular Biology (F. Ausubel et al. eds., 1987 and updated); Essential Molecular Biology (T. Brown ed., IRL Press 1991); Gene Expression Technology (Goeddel ed., Academic Press 1991); Methods for Cloning and Analysis of Eukaryotic Genes (A. Bothwell et al. eds., Bartlett Publ. 1990); Gene Transfer and Expression (M. Kriegler, Stockton Press 1990); Recombinant DNA Methodology (R. Wu et al. eds., Academic Press 1989); PCR: A Practical Approach (M. McPherson et al., IRL Press at Oxford University Press 1991); Cell Culture for Biochemists (R. Adams ed., Elsevier Science Publishers 1990); Gene Transfer Vectors for Mammalian Cells (J. Miller & M. Calos eds., 1987); Mammalian Cell Biotechnology (M. Butler ed., 1991); Animal Cell Culture (J. Pollard et al. eds., Humana Press 1990); Culture of Animal Cells, 2nd Ed. (R. Freshney et al. eds., Alan R. Liss 1987); Flow Cytometry and Sorting (M. Melamed et al. eds., Wiley-Liss 1990); the series Methods in Enzymology (Academic Press, Inc.); Techniques in Immunocytochemistry, (G. Bullock & P. Petrusz eds., Academic Press 1982, 1983, 1985, 1989); Handbook of Experimental Immunology, (D. Weir & C. Blackwell, eds.); Cellular and Molecular Immunology (A. Abbas et al., W.B. Saunders Co. 1991, 1994); Current Protocols in Immunology (J. Coligan et al. eds. 1991); the series Annual Review of Immunology; the series Advances in Immunology; Oligonucleotide Synthesis (M. Gait ed., 1984); and Animal Cell Culture (R. Freshney ed., IRL Press 1987).

As used herein, "a" or "an" means "at least one" or "one or more."

As used herein, "disease or disorder" refers to a pathological condition in an organism resulting from, e.g., infection or genetic defect, and characterized by identifiable symptoms. An example of disease and disorder associated with the musculo-skeletal system is osteoarthritis. Another example of a musculoskeletal disease is degenerative joint disease.

As used herein, "Fc portion," and "Fc region" are well known terms in the art and generally refer synonymously to polypeptides containing the constant region of an immunoglobulin or structural or functional region thereof, such as one or more constant region domains of the immunoglobulin. In one example, the Fc region excludes the first constant region of the immunoglobulin. For example, the Fc region can contain the last two constant region Ig domains of IgA, IgD, or IgG or the last three constant region domains of IgE or IgM. The Fc region further can contain hinge regions. "Fc" can be used to refer to an isolated Fc region polypeptide, or to the Fc region in the context of an antibody, antibody fragment, or Fc fusion protein.

As used herein, "Fc gamma receptor," and "FcγR," refer synonymously to receptors that specifically bind to the Fc region of IgG molecules. The Fc gamma receptors can be naturally-occurring Fc receptors, which are expressed primarily in immune cells, or can be synthetically, e.g. recombinantly, produced Fc receptor polypeptides.

As used herein, a physiological pH is a pH within a range of at or about 7.2 and at or about 8, and typically between at or about 7.4 and at or about 7.9, e.g. 7.2, 7.3, 7.4, 7.5, 7.6, 7.7, 7.8 or 7.9. The particular pH value can be specified.

As used herein, when a protein or portion is directly associated (e.g. bound) to another protein or portion, it is meant that the two proteins/portions associate without the presence of an intermediate, such as a linker or intermediate protein. For example, TGF-beta directly bound to an Ig protein does not contain an LAP intermediate.

"Individual" means any living organism, including humans and other mammals.

By "subject" is meant an organism to which the provided amino acid molecules and complexes and compositions thereof can be administered. In one embodiment, the subject is a mammal or mammalian cell. Mammals include, but are not limited to, humans, and non-human animals, including farm animals, sport animals, rodents and companion animals.

As used herein, "Ig portion" refers to the part of the provided complexes (e.g. the TIGGs) that contain Immunoglobulin protein(s). The Ig portion can contain one or more Ig proteins, which typically are attached to the TGF-beta portion(s) of the complex. Typically, the association between the Ig portion and the TGF-beta portion is via non-covalent bond between the Ig protein(s) and TGF-beta protein(s).

As used herein "immunoglobulin protein" and "Ig protein" refer to whole immunoglobulin molecules and fragments thereof that retain at least part of the functional property of a whole Ig molecule, and in particular retain all or part of the Fc receptor binding affinity and specificity of the whole Ig molecule. For example, the Ig portions of the provided TIGG complexes contain Ig proteins that have all or part of the Fc receptor binding affinity of the corresponding full-length Ig molecules. The Ig proteins include naturally occurring and synthetic proteins, including variants and mimetics of naturally-occurring proteins.

As used herein, "TGF-beta portion" refers to the part of the provided complexes (e.g. the TIGGs) that contain TGF-beta protein(s). The TGF-beta portion can contain one or more TGF-beta proteins, which typically are attached to the Ig-portion(s) of the complex. Typically, the association between the Ig portion and the TGF-beta portion is via non-covalent bond between the Ig protein(s) and TGF-beta protein(s).

As used herein, "TGF-beta" can refer to any TGF-beta protein, including, but not limited to, TGF-beta 1, TGF-beta 2, and TGF-beta 3, including naturally occurring TGF-beta proteins and synthetic proteins, including variants and mimetics. In one provided embodiment, the TGF-beta (e.g. the TGF-beta portion of any of the provided complexes) is a TGF-beta 1, which is a polypeptide growth factor, such as the human TGF-beta 1. For example, in one aspect, the TGF-beta is the human TGF-beta 1 protein having monomers comprising the sequence of amino acids set forth in SEQ ID NO: 1. In another aspect, the TGF-beta is a TGF-beta protein having monomers containing at least at or about, or at or about, 70%, 75%, 80%, 85%, 90%, 95%, 96%, 97%, 98%, 99%, or 100% sequence identity with SEQ ID NO: 1. In another aspect, the TGF-beta includes one or more monomers encoded by a sequence of nucleic acids that encode the polypeptide set forth in SEQ ID NO: 1. In another aspect, the TGF-beta is a TGF-beta protein having one or more monomers encoded by a nucleic acid sequence that encodes a polypeptide containing at least at or about, or at or about, 70%, 75%, 80%, 85%, 90%, 95%, 96%, 97%, 98%, 99%, or 100% sequence identity with SEQ ID NO: 1.

As used herein, when a protein or complex or portion thereof has "TGF-beta activity," an in vivo or in vitro assay (that is known to measure the activity of TGF-beta) of that protein, complex or portion yields a positive result. For example, TGF-beta activity includes the ability to stimulate proliferation, growth, survival and/or differentiation of a cell type that is known to be stimulated by TGF-beta. Also, TGF-beta activity includes the ability to inhibit proliferation, growth, survival and/or differentiation of a cell type that is known to be inhibited by TGF-beta. The activity can be measured in an in vitro or in vivo assay, and can be expressed, for example, as a percentage of the readout of the assay for wild-type TGF-beta, such as TGF-beta dimers containing proteins of the amino acid sequence set forth in SEQ ID NO: 1. Assays for measuring TGF-beta activity are well-known and include cell growth inhibition assays, soft agar assays and radioreceptor assays, and the cell-based PAI-1 promoter assay (wherein the (TGF-beta sensitive) promoter plasminogen activator inhibitor-1 is linked to the luciferase protein coding region and transfected into mink lung epithelial cells. Active TGF-beta is detected in solutions added to the cells in culture via luciferase activity expressed within cells (van Waarde, M A et al., *Anal Biochem* 247(1):45-51, 1997)). In one aspect provided herein, a protein, complex or portion contains at least at or about, or substantially the same, TGF-beta activity compared to a known protein, such as a wild-type TGF-beta. Such a determination is readily made through routine experimentation. An active TGF-beta protein exhibits TGF-beta activity, such as at or about the same, at least at or about the same, or substantially the same activity as a wild-type TGF-beta protein or as one of the TGF-beta proteins provided herein, such as TGF-beta proteins containing the sequence of amino acids set forth in SEQ ID NO: 6.

As used herein, "Transforming Growth Factor-beta-bound IgG" and "TIGG" refer synonymously to complexes containing a TGF-beta portion and an Ig portion, containing TGF-beta protein(s) and Ig protein(s), respectively. The Ig protein(s) are IgG proteins, including full-length Ig molecules of the gamma isotype, and functional portions IgG molecules that retain all or part of the molecule's FcγR binding specificity, such as, but not limited to Fc portions of IgG molecules, and include naturally occurring and synthetic proteins, such as variants. Typically, the TGF-beta portion and the Ig portion are associated via a non-covalent bond. Typically, the TGF-beta portion is a dimer, such as a 25 kDa mature TGF-beta dimer or variant thereof. If it is desired to target receptors that bind to isotypes other than Fc-gamma receptors, any of the TIGGs provided herein can be modified by replacing the IgG portion with an Ig protein(s) of another isotype to create complexes provided herein of other isotypes. Similarly, IgG protein variants in the TIGG complex can include Fc portions of other isotype antibodies that have been modified to render them specific for one or more Fc gamma receptor.

As used herein, when it is generally stated that a polypeptide molecule or region thereof (or a nucleic acid) contains or has "identity" or "homology," per se (without specifying a particular percent identity), to another polypeptide molecule or region thereof (or to another nucleic acid), the two molecules and/or regions share at least at or about 40%, and typically at least at or about 50%, 60% or 70% sequence identity, such as at least at or about 60%, 65%, 70%, 75%, 80%, 85%, 90%, 95%, 96%, 97%, 98%, 99% or 100% sequence identity. The precise percentage of identity can be specified.

Sequence "identity" has an art-recognized meaning. The percentage of sequence identity between two polypeptide or nucleic acid molecules and/or regions can be calculated using well-known and published techniques, such as those described below. In general, for determination of the percentage sequence identity, sequences are aligned so that the highest order match is obtained (see, e.g.: *Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data, Part I*, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991; Carrillo et al. (1988) *SIAM J Applied Math* 48:1073). For sequence identity, the number of conserved amino acids is determined by standard alignment algorithms programs, and can be used with default gap penalties established by each supplier.

The term "identity," when associated with a particular number, represents a comparison between the sequences of a first and a second polypeptide or regions thereof. As used herein, the term at least "90% identical to" refers to percent identities from 90 to 99.99 of one amino acid sequence to the other. Identity of 90% or more is indicative of the fact that, assuming for exemplification purposes, the full length of a first and second polypeptide, each 100 amino acids in length, are compared, no more than 10% (i.e., 10 out of 100) of the amino acids in the first polypeptide differs from that of the second polypeptide. Such differences among the first and second sequences can be represented as point mutations randomly distributed over the entire length of a polypeptide or they can be clustered in one or more locations of varying length up to the maximum allowable, e.g. 10/100 amino acid difference (approximately 90% identity). Differences are defined as amino acid residue substitutions, insertions, additions or deletions. At the level of homologies or identities above about 85-90%, the result should be independent of the program and gap parameters set; such high levels of identity can be assessed readily, often by manual alignment without relying on software.

Sequence identity can be measured along the full length of a polypeptide or nucleic acid molecule or along a region of the molecule. (See, e.g.: *Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data, Part I*, Griffin, A. M., and Griffin, H. G., eds., Humana Press, New Jersey, 1994; *Sequence Analysis in Molecular Biology*, von Heinje, G., Academic Press, 1987; and Sequence Analysis Primer, Gribskov, M. and Devereux, J., eds., M Stockton Press, New York, 1991). While there exists a number of methods to measure identity between two polypeptides, the term "identity" is well known to skilled artisans (Carrillo, H. & Lipman, D., *SIAM J Applied Math* 48:1073 (1988)). Sequence identity compared along the full length of two polypeptides refers to the percentage of identical amino acid residues along the full-length of the molecule. For example, if a polypeptide A has 100 amino acids and polypeptide B has 95 amino acids, which are identical to amino acids 1-95 of polypeptide A, then polypeptide B has 95% identity when sequence identity is compared along the full length of a polypeptide A compared to full length of polypeptide B. Alternatively, sequence identity between polypeptide A and polypeptide B can be compared along a region, such as a 20 amino acid analogous region, of each polypeptide. In this case, if polypeptide A and B have 20 identical amino acids along that region, the sequence identity for the regions would be 100%. Alternatively, sequence identity can be compared along the length of a molecule, compared to a region of another molecule. As discussed below, and known to those of skill in the art, various programs and methods for assessing identity are known to those of skill in the art. High levels of identity, such as 90% or 95% identity, readily can be determined without software.

Whether any two polypeptide or nucleic acid molecules have sequences that contain, or contain at least, a certain percent (e.g. 60%, 70%, 80%, 85%, 90%, 95%, 96%, 97%, 98% or 99%) sequence identity can be determined using known computer algorithms such as the "FASTA" program, using for example, the default parameters as in Pearson et al. (1988) *Proc. Natl. Acad. Sci. USA* 85:2444 (other programs include the GCG program package (Devereux, J., et al., *Nucleic Acids Research* 12(I):387 (1984)), BLASTP, BLASTN, FASTA (Altschul, S. F., et al., *J Molec Biol* 215: 403 (1990); Guide to Huge Computers, Martin J. Bishop, ed., Academic Press, San Diego, 1994, and Carrillo et al. (1988) *SIAM J Applied Math* 48:1073). For example, the BLAST function of the National Center for Biotechnology Information database can be used to determine identity. Other commercially or publicly available programs include DNAStar "MegAlign" program (Madison, Wis.) and the University of Wisconsin Genetics Computer Group (UWG) "Gap" program (Madison Wis.)). The extent of sequence identity (homology) and complementarity may be determined using any computer program and associated parameters, including those described herein, such as BLAST 2.2.2. or FASTA version 3.0t78, with the default parameters. Percent identity further can be determined, for example, by comparing sequence information using a GAP computer program (e.g., Needleman et al. (1970) *J. Mol. Biol.* 48:443, as revised by Smith and Waterman ((1981) *Adv. Appl. Math.* 2:482). Briefly, the GAP program defines similarity as the number of aligned symbols (i.e., nucleotides or amino acids), which are similar, divided by the total number of symbols in the shorter of the two sequences. Default parameters for the GAP program can include: (1) a unary comparison matrix (containing a value of 1 for identities and 0 for non-identities) and the weighted comparison matrix of Gribskov et al. (1986) *Nucl. Acids Res.* 14:6745, as described by Schwartz and Dayhoff, eds., *ATLAS OF PROTEIN SEQUENCE AND STRUCTURE*, National Biomedical Research Foundation, pp. 353-358 (1979); (2) a penalty of 3.0 for each gap and an additional 0.10 penalty for each symbol in each gap; and (3) no penalty for end gaps.

Throughout this disclosure, various provided aspects are presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

A "polynucleotide" refers to a polymeric form of nucleotides of any length, either ribonucleotides or deoxyribonucleotides, or analogs thereof. This term refers to the primary structure of the molecule, and thus includes double- and single-stranded DNA, as well as double- and single-stranded RNA. It also includes modified polynucleotides such as methylated and/or capped polynucleotides.

The terms "nucleic acid" and "nucleic acid sequence" refer to oligonucleotides, nucleotides, polynucleotides, and fragments of any of these, including DNA or RNA (e.g., mRNA, rRNA, tRNA) of genomic or synthetic origin which may be single-stranded or double-stranded and may represent a sense or antisense strand, to peptide nucleic acid (PNA), or to any DNA-like or RNA-like material, natural or synthetic in origin. The term encompasses nucleic acids, i.e., oligonucleotides, containing known analogues of natural nucleotides, naturally occurring nucleic acids, synthetic nucleic acids, and recombinant nucleic acids.

"Recombinant," as applied to a polynucleotide, means that the polynucleotide is the product of various combinations of cloning, restriction and/or ligation steps, and other procedures that result in a construct that is distinct from a polynucleotide found in nature.

As used herein, "substantially pure" means sufficiently homogeneous to appear free of readily detectable impurities as determined by standard methods of analysis, such as thin layer chromatography (TLC), gel electrophoresis and high performance liquid chromatography (HPLC), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art.

As used herein, "biological activity" refers to the in vivo activities of a compound or physiological responses that result upon in vivo administration of a compound, composition or other mixture. Biological activity, thus, encompasses therapeutic effects and pharmaceutical activity of such compounds, compositions and mixtures. Biological activities may be observed in vitro systems designed to test or use such activities.

As used herein, "production by recombinant means" refers to production methods that use recombinant nucleic acid methods that rely on well-known methods of molecular biology for expressing proteins encoded by cloned nucleic acids.

As used herein, "substantially identical" to a product means sufficiently similar so that the property of interest is sufficiently unchanged so that the substantially identical product can be used in place of the product.

As used herein, "equivalent," when referring to two sequences of nucleic acids means that the two sequences in question encode the same sequence of amino acids or equivalent proteins. It also encompasses those that hybridize under conditions of moderate, preferably high stringency, whereby the encoded protein retains desired properties.

As used herein, when "equivalent" is used in referring to two proteins or peptides, it means that the two proteins or peptides have substantially the same amino acid sequence with only conservative amino acid substitutions that do not substantially alter one or more activities or functions of the protein or peptide.

When "equivalent" refers to a property, the property does not need to be present to the same extent [e.g., two peptides can exhibit different rates of the same type of enzymatic activity], but the activities are preferably substantially the same.

The term "substantially" identical or homologous or similar varies with the context as understood by those skilled in the relevant art and generally means at least 70%, preferably means at least 80%, more preferably at least 90%, and most preferably at least 95% identity.

The terms "polypeptide," "peptide," and "protein" are used interchangeably to refer to polymers of amino acids of any length. These terms also include proteins that are post-translationally modified through reactions that include glycosylation, acetylation and phosphorylation.

As used herein, a "fragment thereof" "region thereof" and "portion thereof" refer to fragments, regions and portions that substantially retain at least one function of the full length polypeptide.

The terms "mimetic", peptide mimetic" and "peptidomimetic" are used interchangeably herein, and generally refer to a peptide, partial peptide or non-peptide molecule that mimics the tertiary binding structure or activity of a selected native peptide or protein functional domain (e.g., binding motif, including, but not limited to, Fc portion or region thereof that specifically binds to an Fc receptor). Peptide mimetics include recombinantly and chemically modified peptides, and non-peptide agents. Knowing the binding and structural features of the provided TIGG complexes and proteins thereof, one of skill in the art can design peptidomimetics having equivalent, or substantially equivalent, structure and/or function, such as, for example, the same, about the same, or greater binding affinity compared to a given molecule or complex, such as compared to a native IgG molecule. The mimetics include those entirely composed of synthetic, non-natural analogues of amino acids, and chimeric molecules composed of natural peptide amino acids and non-natural analogs of amino acids. The mimetics further include polypeptide incorporating conservative amino acid substitutions, as long as such substitutions also do not substantially alter the mimetic's structure and/or activity. The polypeptides and peptides provided herein, and polypeptides and peptides used in the provided complexes, compositions, combinations and methods, can contain "mimetic" ("peptidomimetic") forms.

As used herein, a variant of a polypeptide (protein) or polynucleotide (namely a parent polypeptide or polynucleotide) is a protein or polynucleotide that contains one or more alterations in the amino acid or nucleic acid sequence, respectively, compared to the amino acid sequence of the parent polypeptide or the nucleic acid sequence of the parent polynucleotide. Alterations in sequences include substitutions, including conservative substitutions, deletions, additions and insertions, compared to the sequence of the polypeptide or polynucleotide of interest. A "conservative" amino acid substitution is a substitution of an amino acid having similar structural or chemical property compared to the corresponding amino acid in the parent polypeptide. Non-conservative amino acid substitutions are those where the charge, hydrophobicity and/or bulk of the amino acid is substantially altered. Typically, a variant polypeptide has at least 75% sequence identity, and preferably at least 80%, 85%, 90%, 95%, or 95% sequence identity sequence identity, to the basic sequence. There may be at least 80%, for example at least 85%, 90% or 95%, amino acid identity over a stretch of 40 or more, for example 60, 80, 100 or more, contiguous amino acids ("hard homology").

Variants of polypeptides may be generated by conventional techniques, including either random or site-directed mutagenesis of DNA encoding the polypeptide. The resultant DNA fragments are then cloned into suitable expression hosts such as *E. coli* or mammalian cells using conventional technology and clones that retain the desired activity are detected. The term "variant" also includes naturally occurring allelic variants. For example, TGF-beta 1, TGF-beta 2 and TGF-beta 3 are all variants for the purposes of this application, in that their amino acid sequences are greater than 85% identical.

The variants and mimetics can be described in terms of the degree of amino acid or nucleotide sequence identity compared to the parent polypeptide or polynucleotide. For example, variants include polypeptides and polynucleotides with at least at or about 50%, 60%, and typically at least at or about 70%, 80%, 90%, 91%, 92%, 93%, 94%, 95%, 96%, 97%, 98%, 99% or more sequence identity to the parent polypeptide or polynucleotide. Typically, the variants further retain a substantial amount of one or more structural or functional properties of the parent polypeptide or polynucleotide, or compared to another reference polypeptide or polynucleotide such as a wild-type protein or polynucleotide (e.g. a wild-type IgG or TGF-beta protein). The particular property can be specified, along with the desired similarity to the parent or other protein. For example, the TGF-beta-Ig complexes (e.g. TIGG) and portions thereof include variants (e.g. variants having a particular sequence identity to a parent molecule) that have a substantially similar, greater, or lower binding affinity for a particular FcR compared to a different molecule or complex, such as a wild-type protein (e.g. a wild-type IgG molecule).

For members of a class of variants defined as having a particular percent identity or at least a particular percent identity, routine experimentation can be used to determine that the variant is within the scope of the provided embodiment, i.e., that the member of the class has a particular function or structure, e.g. binding affinity, for example, that the structure and/or function is not substantially altered compared to the parent polypeptide or polynucleotide or other molecule.

"Derivative" refers to a polypeptide or polynucleotide that has been derived from a parent polynucleotide or polypeptide the basic sequence by modification, for example by conjugation or complexing with other chemical or protein moieties or by post-translational modification techniques as would be understood in the art. Such derivatives include amino acid deletions and/or additions to polypeptides or variants thereof wherein said derivatives retain activity of the basic protein. Other derivatives include modification to side chains, incorporation of unnatural amino acids and/or their derivatives during peptide, polypeptide or protein synthesis and the use of crosslinking agents.

As used herein, a "composition" refers to any mixture of two or more products or compounds. It may be a solution, a suspension, liquid, powder, a paste, aqueous, non-aqueous or any combination thereof.

"Therapeutic composition" is defined as comprising TIGG and a pharmaceutically acceptable carrier.

As used herein, "potency" is a measure of the relative amount of a composition required to produce a specific effect; the more potent the composition, the smaller the amount required to produce the effect.

As used herein, a "combination" refers to any association between two or among more items.

As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. See e.g., REMINGTON: THE SCIENCE AND PRACTICE OF PHARMACY 20th Ed. (Lippincott, Williams & Wilkins 2003). Except insofar as any conventional media or agent is incompatible with the active compound, such use in the compositions is contemplated.

The term "therapeutically effective amount" as used herein, means that amount of TIGG that elicits the biological or medicinal response in a tissue system, animal or human that is being sought by a researcher, veterinarian, medical doctor or other clinician, which includes alleviation of one or more symptoms of the disease or disorder being treated, e.g., treatment, healing, prevention or amelioration of the relevant medical condition, or an increase in rate of treatment, healing, prevention or amelioration of such conditions. When applied to an individual active ingredient administered alone, a therapeutically effective dose refers to that ingredient alone. When applied to a combination, a therapeutically effective dose refers to combined amounts of the active ingredients that result in the therapeutic effect, whether administered in combination, serially or simultaneously.

The total dose required for each treatment can be administered by multiple doses or in a single dose. The pharmaceutical composition can be administered alone or in conjunction with other pharmaceuticals directed to the pathology, or directed to other symptoms of the pathology.

B. TGF-Beta Proteins, Complexes Containing TGF-Beta Proteins, and Methods of Use Methods and compositions are needed to target and treat musculoskeletal diseases such as osteoarthritis. In particular, therapies are needed that ameliorate pain and cartilage destruction associated with osteoarthritis. It has been suggested that TGF-beta proteins may have considerable benefit in cartilage repair (E. N. Blaney Davidson, P. M. van der Kraan and W. B. van den Berg, *OsteoArthritis and Cartilage* (2007) 15, 597-604.)

Available TGF-beta proteins, however, are limited. For example, available TGF-beta proteins can have low potency and activity, and can have relatively short half-lives in vivo.

The provided TGF-beta proteins and complexes overcome these limitations. Among the provided proteins and complexes are targeted proteins and complexes (e.g. dimers and multimers), for example, TGF-beta proteins complexed (e.g. non-covalently bound) to other proteins, such as immunoglobulin molecules and portions thereof. The provided proteins and complexes can stimulate cartilage growth and chondrocyte differentiation.

Cells targeted by the provided proteins include, but are not limited to, cells at the site of administration that possess functional FcγR. Alternatively, the targeted cells are cells that encounter the proteins or complexes in vivo within the synovium, such as chondrocytes or mesenchymal stem cells that can differentiate into chondrocytes. In one aspect, the provided proteins and complexes are injectable therapeutic protein complexes.

Also provided are compositions (e.g. pharmaceutical compositions) and combinations containing the proteins and complexes, and therapeutic formulations of the complexes. The pharmaceutical compositions include, but are not limited to, compositions containing TGF-beta-bound immunoglobulin and a pharmaceutically acceptable carrier, and compositions containing a vector with a polynucleotide that encodes a TGF-beta-bound immunoglobulin in admixture with a pharmaceutically acceptable carrier.

The proteins, complexes, compositions and combinations can be used in treating and diagnosing various therapeutic indications. For example, the provided complexes and compositions can be used to treat diseases, such as osteoarthritis. Also provided are methods for producing the proteins and complexes, and methods for their use, for example, in disease treatment and diagnosis. For example, provided are methods for treating osteoarthritis in a subject, comprising administering a therapeutically effective amount of the provided pharmaceutical composition to a subject. The provided pharmaceutical compositions can be used to osteoarthritis in vitro or in vivo.

i. TGF-Beta

TGF-beta proteins are members of a superfamily of structurally similar regulatory proteins, including, but not limited to, the mammalian TGF-beta 1, 2, and 3, and active/inhibin and bone morphogenic proteins. Mature TGF-beta typically exists as a homodimer, such as the dimeric mature TGF-beta molecule, containing two covalently associated TGF-beta molecules. TGF-beta proteins further include latent TGF-beta complexes, such as complexes containing latency-associated proteins (LAP). For example, the latent complexes include the naturally occurring inactive complex containing two covalently linked latency-associated proteins (LAP) non-covalently linked to the dimeric mature TGF-beta molecule, which can be activated by dissociation of the LAP or by conformational changes in the complex, such as by binding of LAP to either thrombospondin or $\alpha v \beta 6$ integrin.

Active TGF-beta dimers can specifically bind to TGF-beta Receptor II (TGF-beta RII), and typically bind two TGF-beta RII molecules. Binding by the TGF-beta homodimer recruits two TGF-beta Receptor I (TGF-beta RI) molecules, forming a heteromeric complex. Downstream signaling is mediated by the bound TGF-beta RI, a serine-threonine kinase, which is phosphorylated upon complexation to the TGF-beta/TGF-beta RII complex. Activation of TGF-beta RI causes phosphorylation of Smad2 and Smad3 and induces their heterodimerization with Smad4. The activated Smad complex then translocates to the nucleus where it regulates gene transcription.

TGF-beta regulates a plurality of processes, including cell differentiation and proliferation, migration, motility, deposition of the extracellular matrix, cell death, and immunosuppression. TGF-beta signaling can increase the synthesis of matrix proteins, such as vitronectin, fibronectin, laminin, tenascin, proteoglycans, and collagens, enhance the expression of cell adhesion molecules such as integrins, and increase the synthesis of various protease inhibitors. It also can decrease the synthesis of matrix degrading proteases.

Active TGF-beta proteins have immunosuppressive activities, for example, having inhibitory effects on several major immune system cell types, including T-cells (both $CD4^+$ and $CD8^+$), B lymphocytes, monocytes, macrophages, dendritic cells, polymorphonuclear leukocyte. Additionally, active TGF-beta can be a powerful chemoattractant for a plurality of types of immune cells, including T-cells (both $CD4^+$ and $CD8^+$), monocytes, PMNs, neutrophils and mast cells. TGF-beta is also a strong anabolic factor for both cartilage growth and retention.

ii. Immunoglobulins and Fc Receptors

In one embodiment, the provided TGF-beta complexes (e.g. dimers and multimers) have Ig portions that contain Immunoglobulin (Ig) molecules (Ig proteins), including, but not limited to, IgG molecules, and portions of Ig molecules, such as Fc regions of IgG molecules.

Variable regions of Ig molecules (and in particular, complementary-determining regions (CDRs)) contribute to antigen specificity and binding. Ig constant regions, on the other hand, are less variable among different immunoglobulin (Ig) molecules and serve other functions, including antibody effector functions. Natural full-length Ig molecules contain between three and four constant region Ig domains. The constant region of a full-length immunoglobulin includes an Fc region, which typically includes the constant region domains, excluding the first constant region domain. Immunoglobulins of a particular isotype (classes: IgG, IgM, IgA, IgE, IgD and sub-classes thereof) can be characterized by particular effector functions and constant regions having similar basic structures/sequences. Human Ig classes and subclasses include IgG (including IgG1, IgG2, IgG3, IgG4), IgM, IgA (including IgA1, IgA2), IgE and IgD.

Fc receptors are cell surface receptors, expressed on various immune cell types, which specifically bind Fc regions of immunoglobulin molecules. Fc receptors are generally categorized according to the class of Ig molecule they recognize. For example, Fc gamma receptors (FcγR) bind Fc portions of IgG molecules.

iii. Complexes, Including TGF-Beta—IgGs (TIGGs)

Among the provided proteins and complexes are TGF-beta-IgGs (TIGGs), which are proteins and complexes containing a TGF-beta portion (containing one or more TGF-beta protein, such as a TGF-beta dimer) associated with an Ig portion (containing one or more Ig protein). For example, the provided TIGGs include those containing one, or more than one, IgG molecule bound to a TGF-beta, for example, to a TGF-beta dimer. The TGF-beta protein(s) typically are associated with the Ig protein(s) via non-covalent bond. The Ig proteins include full-length immunoglobulins, such as IgG, and functional regions and portions of full-length Ig molecules, such as constant regions and Fc regions and functional portions thereof. The provided compositions include isolated TIGGs, such as, but not limited to, isolated multimer complexes in which the 25 kD dimeric protein TGF-beta 1 is noncovalently bound to an immunoglobulin G protein or to two immunoglobulin G proteins.

a. Naturally Occurring and Purified TGF-Beta—IgG Complexes

Naturally-occurring TGF-beta bound IgG in vivo has been reported. For example, complexes containing TGF-beta and IgG were isolated from the MRL/lpr mouse model of systemic lupus erythematosis (Caver, T E, et al., J Clin Invest 98(11):2496-2506 (1996)) and the B16 melanoma mouse model (Harada et al., Clin Exp Immunol 128:204-212 (2002)). Further, IgG fractions, isolated from two SLE patients during active disease, were consistent with TGF-beta-bound IgG.

Most reports of naturally occurring TGF-beta-bound IgG have suggested that the association of the two proteins occurs through a latency-associated protein (LAP) intermediate. The latent, inactive form of TGF-beta contains two LAP molecules non-covalently bound to and inactivating the dimeric, mature TGF-beta. The various suggestions that IgG bound TGF-beta complex contained LAP were based on the detection of LAP and inactive properties of the complexes. One study reported that TGF-beta bound IgG, isolated from mouse plasma, remained inactive unless incubated at acidic pH (Stach and Rowley, ibid). Other studies, however, have reported TGF-beta-LAP-IgG complexes with TGF-beta in an active conformation. Another study detected LAP produced by the same B-cells that actively produced TGF-beta-bound IgG (Rowley, D A and Stach, R M, Int Immunol, 10(3):355-363, 1998). Another report (Caver et al., ibid) concluded that naturally occurring TGF-beta IgG complexes must contain LAP, based on unsuccessful attempts at binding recombinant or plasma derived TGF-beta (both devoid of LAP) to purified mouse IgG.

Dimeric TGF-beta bound to soluble IgG without an intermediary binding protein (e.g., TGF-beta latency associated protein (LAP)), has not been reported. Bouchard and colleagues did report binding of free TGF-beta dimer to the non-CDR portion of an IgG molecule immobilized on a column (Bouchard et al., J Exp Med, 182:1717-1726, 1995). In this report, TGF-beta purified from porcine platelets was incubated at 4° C. for 18 hours with insoluble rabbit IgG immobilized on a Sepharose column. Based on elution of TGF-beta from the sepharose column after washing, it was determined that the free TGF-beta had associated with the IgG. Others, however, were unable to extend this study to bind TGF-beta to IgG in a soluble format (Caver et al. (ibid)).

Purified, naturally occurring IgG-bound TGF-beta had suppressive activity in vitro on cytolytic T lymphocyte function (Stach, R M and Rowley, D A, J Exp Med, 178:841-852, 1993), B lymphocyte function (Bouchard et al., J Exp Med, 182:1717-1726, 1995), polymorphonuclear leukocytes (PMN) function (Caver, T E, et al., J Clin Invest, 98(11):2496-2506, 1996), and antigen presenting cell (APC) function (Harada et al., Clin Exp Immunol, 128:204-212, 2002). The inhibition of cytolytic T lymphocyte responses by IgG-bound TGF-beta was dependent on the presence of macrophages with functional Fc receptors (Stach, R M and Rowley, D A, J Exp Med, 178:841-852, 1993). IgG-bound TGF-beta was approximately 500 times more potent in suppression of PMN function than recombinant TGF-beta (Caver, T E, et al., J Clin Invest, 98(11):2496-2506, 1996).

The provided protein complexes include TGF-beta proteins associated with IgG molecules or portions thereof (e.g. portions containing the Fc region of an IgG molecule), for example, via non-covalent bond b. TGF-Beta Portions of the Provided Complexes The provided TIGG complexes contain TGF-beta portions, which contain one or more TGF-beta protein, such as one or two or more TGF-beta proteins, for example, a dimer. The TGF-beta proteins include naturally occurring TGF-beta, and synthetic TGF-beta proteins, including variants, fragments, and mimetics retaining TGF-beta activity. The TGF-beta portion contains one or more TGF-beta protein or TGF-related protein, such as TGF-beta variants, including variants retaining at least at or about or at or about 50%, 60%, 70%, 80%, 90%, 95%, 96%, 97%, 98%, 99%, 100% or greater than at or about 100% of the level of activation of the TGF-beta cascade compared to a wild-type TGF-beta homodimer, such as the TGF-beta homodimer containing monomers encoded by the polypeptide of SEQ ID NO: 1. Methods for measuring activation of the TGF-beta cascade are well known.

Methods for assaying the activity of TGF-beta in a sample are well known. Exemplary methods include assays for cell growth and/or viability (e.g., apoptosis assays) of cells sensitive to TGF-beta treatment. For example, growth of the mink lung epithelial cell line (ATCC® Number CCL-64), which is generally accepted for use in such assays, is inhibited by TGF-beta concentrations down to the picogram (pg)/ml range (see Meager, A., J. Immunol. Methods, 141:1-14 (1991)). Methods to assay cell growth and viability are well known. Assays for TGF-beta activity can be used, for example, to measure activity of TGF-beta protein samples for preparation of the provided complexes.

In some examples, a TGF-beta activity assay is used to assess the integrity and/or purity of the TIGG complexes, for example, by measuring the presence and/or relative amount of free TGF-beta (which binds to TGF-beta receptors to inhibit growth or viability) compared to the presence or amount of intact TIGG complexes (not binding to TGF-beta receptors), and by assessing the ability of such complexes to dissociate into free TGF-beta and immunoglobulin, e.g., upon treatment with acid.

The TGF-beta proteins of the provided TIGGs include, but are not limited to, the three known TGF-beta isoforms produced in mammals, TGF-beta 1, TGF-beta 2, TGF-beta 3. The TGF-beta proteins include monomers, and typically are dimers. For example, the TGF-beta portion of the TIGGs include, but are not limited to, TGF-beta homodimers, such as the dimeric mature TGF-beta molecule, containing two covalently associated TGF-beta molecules.

In one embodiment, the TGF-beta protein is a TGF-beta 1, which is a polypeptide growth factor, including, but not limited to, human TGF-beta 1. For example, in one aspect, the TGF-beta is the human TGF-beta 1 protein having the sequence of amino acids set forth in SEQ ID NO: 1, or a TGF-beta 1 dimer, where each monomer of the dimer contains the sequence of amino acids set forth in SEQ ID NO: 1. In another aspect, the TGF-beta is a TGF-beta protein having at least at or about 70%, 75%, 80%, 85%, 90%, 95%, 96%, 97%, 98%, 99%, or 100% sequence identity with SEQ ID NO: 1, or having at or about 70%, 75%, 80%, 85%, 90%, 95%, 96%, 97%, 98%, 99%, or 100% sequence identity with SEQ ID NO: 1. In another aspect, the TGF-beta is a TGF-beta dimer, where each monomer of the dimer is a protein having at least at or about 70%, 75%, 80%, 85%, 90%, 95%, 96%, 97%, 98%, 99%, or 100% sequence identity with SEQ ID NO: 1, or having at or about 70%, 75%, 80%, 85%, 90%, 95%, 96%, 97%, 98%, 99%, or 100% sequence identity with SEQ ID NO: 1. In one example, the two monomers of the TGF-beta dimer are associated via a covalent bond, e.g. a disulfide bond. For example, exemplary of the TGF-beta proteins are TGF-beta dimers comprising two monomers bound by a covalent disulfide bond, each monomer of the dimer having at or about 80% or higher sequence identity to the amino acid sequence of SEQ ID NO:1.

In another aspect, the TGF-beta protein (e.g. each monomer of a TGF-beta dimer in the TGF-beta portion), contains one or more amino acid substitutions, deletions, insertions or additions relative to SEQ ID NO:1, where the TGF-beta portion of the TIGG retains essentially the same binding and activation profile as a wild-type TGF-beta monomer, such as the TGF-beta monomer of SEQ ID NO: 1. For example, in one aspect, the TGF-beta portion of the TIGG retains at least 50%, 60%, 70%, 80%, 90%, 95%, 96%, 97%, 98%, 99% or 100% of the binding affinity to a mammalian TGF-beta type II Receptor in comparison to a wild-type TGF-beta monomer.

In another aspect, the TGF-beta is encoded by a sequence of nucleic acids encoding the sequence of amino acids set forth in SEQ ID NO:1. In another aspect, the TGF-beta is a TGF-beta 1 dimer, where each monomer is encoded by a sequence of nucleic acids encoding the sequence of amino acids set forth in SEQ ID NO:1. In another aspect, the TGF-beta is encoded by a sequence of nucleic acids encoding a sequence of amino acids having at least at or about 70%, 75%, 80%, 85%, 90%, 95%, 96%, 97%, 98%, 99%, or 100% sequence identity, or at or about 70%, 75%, 80%, 85%, 90%, 95%, 96%, 97%, 98%, 99%, or 100% sequence identity, with SEQ ID NO:1. In another aspect, the TGF-beta is a dimer, where each monomer of the dimer is a encoded by a sequence of nucleic acids encoding a polypeptide having at least at or about 70%, 75%, 80%, 85%, 90%, 95%, 96%, 97%, 98%, 99%, or 100% sequence identity, or at or about 70%, 75%, 80%, 85%, 90%, 95%, 96%, 97%, 98%, 99%, or 100% sequence identity, with SEQ ID NO:1. In one example, the two monomers of the TGF-beta dimer are associated via a covalent bond, e.g., a disulfide bond. For example, exemplary of the TGF-beta proteins are TGF-beta dimers comprising two monomers bound by a covalent disulfide bond, each monomer of the dimer having at or about 80% or higher sequence identity to the amino acid sequence of SEQ ID NO:1.

In another aspect, the TIGG has a similar activation of the TGF-beta cascade in comparison to wild-type TGF-beta. In one example, the activation retains at least at or about or at or about 50%, 60%, 70%, 80%, 90%, 95%, 96%, 97%, 98%, 99%, 100% or greater than at or about 100% of the level of activation shown by a wild-type TGF-beta homodimer.

c. Immunoglobulin Portions of the Complexes

The TGF-beta protein(s) in the TGF-beta portions of the TIGGs are associated with protein(s) of Immunoglobulin (Ig) portions. The Ig portions contain one or more Ig protein, such as one or two or more Ig molecule, chain or fragment thereof. The Ig proteins include Ig molecules, and chains and functional portions (e.g. fragments) thereof. For example, in one aspect, the Ig portion contains a full-length immunoglobulin. In another aspect, the Ig portion contains one or more chains of the full-length immunoglobulin (typically an IgG molecule), such as heavy chains. In another aspect, the Ig portion contains a functional portion of a full-length immunoglobulin or chain, such as a constant region or Fc region thereof (typically an Fc-gamma region). The constant region or Fc region thereof contains all or part of the binding affinity to one or more Fc receptors, compared to the corresponding full-length Ig molecule. In one embodiment, the Ig portion contains one Ig protein, which can be a full-length Ig molecule or a region thereof. In another embodiment, the Ig portion contains more than one, e.g. 2 or more, Ig proteins, each of which is a full-length Ig molecule or region thereof. In one example, the Ig portion contains two Ig proteins, each of which is associated with one monomer of the TGF-beta dimer in the TIGG complex. The Ig proteins can be human Ig proteins, or any mammalian Ig proteins, such as mouse or rat Ig proteins. For use in human subjects, it typically is desired that the Ig proteins are human Ig proteins.

In one aspect, the Ig portion of the TIGG is or contains a full-length immunoglobulin G molecule, containing two heavy chains and two light chains, the two heavy chains being covalently bound to one another via disulfide bonds, and each of the two light chains covalently attached to one of the heavy chains. In another aspect, the Ig portion of the TIGG is less than the full length IgG molecule, such as a portion of the IgG molecule that retains all or part of the binding specificity for one or more of the Fc receptors bound by the constant region of the IgG molecule. The Ig proteins of the Ig portions include natural Ig molecules (and regions thereof) and synthetically produced, e.g. artificial, Ig molecules and portions, such as variant Ig proteins that vary in amino acid sequence compared to a wild-type Ig protein or any of the Ig proteins disclosed herein, and have particular desired functional characteristics, such as binding affinities for particular Fc receptors.

The Ig proteins of the Ig portions can be of any isotype and/or sub-class, and typically is of the IgG isotype. The Ig portion of a single complex, e.g. a single TIGG, can contain more than one distinct isotype/sub-type. Also provided are mixtures of TIGGs, which can contain multiple different Ig isotypes and sub-types. The IgG proteins thereof include, but are not limited to, human IgG1, human IgG2, human IgG3, human IgG4, canine IgG1, canine IgG2, canine IgG3 and canine IgG4, and functional portions of such IgG molecules, including Fc portions, and variants thereof, such as those having substantially the same, or improved binding affinities/specificities as described herein.

For example, the Ig proteins include, but are not limited to, proteins containing the sequence of amino acids (e.g. proteins having an Fc region containing the sequence of amino acids) set forth in any of: SEQ ID NO: 2, SEQ ID NO: 3, SEQ ID NO: 4, and SEQ ID NO: 5 and the Ig proteins having the amino acid sequences set forth in Table 1, and variants thereof, such as those having one or more addition, deletion, substitution or insertion, and having have desired functional characteristics as described herein. For example, the Ig proteins include proteins with amino acid sequences (and those with Fc regions having amino acid sequences) containing at least at or about, or at or about, 70%, 75%, 80%, 85%, 90%, 95%, 96%, 97%, 98%, 99%, or 100% sequence identity to any of SEQ ID NO: 2, SEQ ID NO: 3, SEQ ID NO: 4, and SEQ ID NO: 5, and Ig proteins with amino acid sequences containing at least at or about, or at or about, 70%, 75%, 80%, 85%, 90%, 95%, 96%, 97%, 98%, 99%, or 100% sequence identity to any of the Ig proteins set forth in Tables 1 and 2.

In another embodiment, the Ig protein is encoded by a polynucleotide, where the polynucleotide encodes the amino acid sequence set forth in any of: SEQ ID NO: 2, SEQ ID NO: 3, SEQ ID NO: 4, and SEQ ID NO: 5, or encodes an amino acid sequence containing at least at or about, or at or about, 70%, 75%, 80%, 85%, 90%, 95%, 96%, 97%, 98%, 99%, or 100% sequence identity to any of SEQ ID NO: 2, SEQ ID NO: 3, SEQ ID NO: 4, and SEQ ID NO: 5, or encodes an amino acid sequence containing at least at or about, or at or about, 70%, 75%, 80%, 85%, 90%, 95%, 96%, 97%, 98%, 99%, or 100% sequence identity to any of the Ig proteins set forth in Tables 1 and 2.

The Ig portions, including the Ig portions containing variant Ig proteins, have a desired functional property, typically at or about specified binding affinity, or at least at or about a specified binding affinity, to one or more Fc receptors or Fc receptor classes. The binding affinity can be specified as a percentage of the binding affinity of a known (e.g. wild-type) Ig molecule or region thereof, or can be specified as a ratio of the binding affinity for a particular type of Fc receptor compared to another type.

For example, in one aspect, the Ig portion of the TIGG contains an Ig protein that is a variant of a known Ig molecule, such as those having any of the amino acid sequences described herein, that retains all or part of the binding specificity of the parent Ig protein for one or more of the Fc receptors bound by the constant region of the IgG molecule, such as at least at or about 50%, 60%, 70%, 80%, 90%, 95%, 96%, 97%, 98%, 99% or 100% of the binding affinity of the parent Ig protein, constant region, or Fc region, for example, to a mammalian FcγR. For example, the Ig portions include those having a particular sequence identity to any of SEQ ID NOs: 2-5, and having at least at or about 50%, 60%, 70%, 80%, 90%, 95%, 96%, 97%, 98%, 99% or 100% of the binding affinity of those Ig proteins for a specified FcγR.

In certain aspects, the derivative, variant or fragment thereof retains at least 50%, 60%, 70%, 80%, 90%, 95%, 96%, 97%, 98%, 99% or 100% of the binding affinity of the full-length Ig, constant region, or Fc region to a mammalian FcγR.

Variants

The Ig portions of the provided TIGGs further include Ig proteins that are variants of known proteins (e.g. wild-type Ig molecules and any of the proteins described herein) that retain all or part of the function of the parent proteins, and/or contain improved function compared to the parent.

Multiple Ig Sub-Types and TIGG Mixtures

In one embodiment, the Ig portion contains one Ig subtype. In another embodiment it contains multiple sub-types. In another embodiment, provided is a TIGG mixture, containing a plurality of different TIGGs, having different Ig classes and/or sub-types. In one aspect of this embodiment, the TIGG mixture includes a mixture of two, three or all four naturally occurring human immunoglobulin G subtypes in the Ig portions of the plurality of TIGGs in the mixture. Such mixtures include those made by combining the mixture of Ig molecules contained in the commercially available well-known human gamma globulin used for intravenous injection in humans or similar mixture. This composition can be used, for example, in treatment of osteoarthritis. In another aspect, the TIGG mixture composition contains, as the Ig portions of the TIGGs, any one or more of purified human IgG1, human IgG2, IgG3 or human IgG4. Exemplary of such a composition is a TIGG composition for treating osteoarthritis. In another aspect, the TIGG composition contains, as the Ig portions of the TIGGs, the Fc region (Fc fragment) or functional region thereof, of any one or more of human IgG1, IgG2, IgG3 or IgG4 Exemplary of such a composition is a TIGG composition for treating osteoarthritis.

In another aspect, the TIGG composition contains, as the Ig portions of the TIGGs, the Ig portions of human gamma globulin (available commercially as IVIG).

d. Association of the TGF-Beta and Ig Portions of the Complex

The TGF-beta portion (for example, the 25 kDa TGF-beta dimer), associates with the Ig portion (e.g. the IgG molecule or Fc portion thereof) in the provided complexes. Typically, the association is via an interaction (typically a direct interaction) of the TGF portion with the constant region of the Ig molecule(s) in the Ig portion, such as via interaction with the Fc portion. In another aspect, the TGF-beta portion can associate with the Ig portion through the variable region of the Ig, such as by interacting with one or more CDR of the variable region. Various methods for association of proteins in complexes are well known and can be used to associate the TGF-beta portion with the Ig portion in the provided complexes. Typically, however, the TGF-beta portion of the provided complexes, for example, the TIGG, is associated with the Ig portion via a bond, and typically via a non-covalent bond. Methods for forming the complexes are described herein. Alternatively, the two molecules can be associated via another well-known method or interaction, such as via a linker, such as a peptide linker.

Exemplary immunoglobulin proteins and nucleic acid sequences that can be used in the compositions and methods described herein, include, but are not limited to, the sequences described in Table 1.

TABLE 1

Ig Proteins for use in TIGGs

| GenBank gi No. | Accession No. | DESCRIPTION | SPECIES |
|---|---|---|---|
| 184747 | AAC82527 | immunoglobulin, Fc region | Homo sapiens |
| 184758 | AAB59393 | immunoglobulin G2, Fc region | Homo sapiens |
| 577056 | CAA27268 | immunoglobulin G3, Fc region | Homo sapiens |
| 184759 | AAB59394 | immunoglobulin G4, Fc region | Homo sapiens |
| 17066523 | AF354264 | immunoglobulin, Fc region | Canis familiaris |
| 9858135 | AAG01011 | immunoglobulin, Fc region | Equus caballus |
| 3402542 | AB016710 | immunoglobulin, Fc region | Felis catus |
| 109133449 | XP_001097387 | immunoglobulin, Fc region | Macaca mulatta |
| 109085083 | XP_001100439 | immunoglobulin, constant region heavy chain | Macaca mulatta |
| 109133460 | XP_001099592 | immunoglobulin, constant region, heavy chain | Macaca mulatta |
| 114655149 | XP_522970 | immunoglobulin, Fc region | Pan troglodytes | vi. Polynucleotides

Also provided are nucleic acids, e.g., polynucleotides, encoding the TIGGs and proteins and portions thereof. The polynucleotides include any polynucleotide encoding a TGF-beta protein described herein, such as polynucleotides encoding a TGF-beta protein having the sequence of amino acids set forth in SEQ ID NO:1, and polynucleotides containing one or more nucleotide addition, deletion, insertion or substitution compared to such a polynucleotide, but still encoding a polypeptide having one or more functional properties of such a protein, for example, retaining all or a substantial portion of the TGF-beta activity compared to the protein or compared to wild-type TGF-beta. For example, the polynucleotides encode amino acid sequences including those having at least at or about 70, 75, 80, 85, 90, 91, 92, 93, 94, 95, 96, 97, 98, 99 or 100% sequence identity to SEQ ID NO:1.

The provided polynucleotides further include polynucleotides encoding any of the Ig proteins and variants described herein, such as polynucleotides encoding an Ig protein having the sequence of amino acids set forth in any of: SEQ ID NO:2, SEQ ID NO:3, SEQ ID NO:4, and SEQ ID NO:5 and, polynucleotides of Table 1. The Ig polynucleotides further include variants of these polynucleotides, such as those having one or more addition, deletion, substitution or insertion, and having have desired functional characteristics as described herein.

In certain aspects, the polynucleotides encode Ig protein variants or fragments thereof that retain at least 50%, 60%, 70%, 80%, 90%, 95%, 96%, 97%, 98%, 99% or 100% of the binding affinity of the full-length Ig, constant region, or Fc region to a mammalian FcγR.

The nucleic acids used to practice the provided embodiments can be isolated from a variety of sources, genetically engineered, amplified, and/or expressed/generated recombinantly. Recombinant polypeptides generated from these nucleic acids can be individually isolated or cloned and tested for a desired activity. Any recombinant expression system can be used, including bacterial, mammalian, yeast, insect or plant cell expression systems.

Alternatively, these nucleic acids can be synthesized in vitro by well-known chemical synthesis techniques, as described in, e.g., Adams (1983) *J. Am. Chem. Soc.* 105:661; Belousov (1997) *Nucleic Acids Res.* 25:3440-3444; Frenkel (1995) *Free Radic. Biol. Med.* 19:373-380; Blommers (1994) *Biochemistry* 33:7886-7896; Narang (1979) *Meth. Enzymol.* 68:90; Brown (1979) *Meth. Enzymol.* 68:109; Beaucage (1981) *Tetra. Lett.* 22:1859; U.S. Pat. No. 4,458,066. Alternatively, nucleic acids can be obtained from commercial sources.

Techniques for the manipulation of nucleic acids, such as, e.g., subcloning, labeling probes (e.g., random-primer labeling using Klenow polymerase, nick translation, amplification), sequencing, hybridization and the like are well described in the scientific and patent literature, see, e.g., Sambrook, ed., *Molecular Cloning: A Laboratory Manual* (2nd ed.), Vols. 1-3, Cold Spring Harbor Laboratory, (1989); *Current Protocols in Molecular Biology*, Ausubel, ed. John Wiley & Sons, Inc., New York (1997); *Laboratory Techniques in Biochemistry and Molecular Biology: Hybridization with Nucleic Acid Probes, Part I. Theory and Nucleic Acid Preparation*, Tijssen, ed. Elsevier, N.Y. (1993).

Another useful means of obtaining and manipulating nucleic acids used to practice the provided methods is to clone from genomic samples, and, if desired, screen and re-clone inserts isolated or amplified from, e.g., genomic clones or cDNA clones.

Sources of nucleic acid used in the provided include genomic or cDNA libraries contained in, e.g., mammalian artificial chromosomes (MACs), see, e.g., U.S. Pat. Nos. 5,721,118; 6,025,155; human artificial chromosomes, see, e.g., Rosenfeld (1997) *Nat. Genet.* 15:333-335; yeast artificial chromosomes (YAC); bacterial artificial chromosomes (BAC); P1 artificial chromosomes, see, e.g., Woon (1998) *Genomics* 50:306-316; P 1-derived vectors (PACs), see, e.g., Kern (1997) *Biotechniques* 23:120-124; cosmids, recombinant viruses, phages or plasmids.

In practicing the provided embodiments, provided nucleic acids can be reproduced by amplification. Amplification can also be used to clone or modify the provided nucleic acids. Thus, provided are amplification primer sequence pairs for amplifying the provided nucleic acids. One of skill in the art can design amplification primer sequence pairs for any part of or the full length of these sequences.

Amplification reactions can also be used to quantify the amount of nucleic acid in a sample (such as the amount of message in a cell sample), label the nucleic acid (e.g., to apply it to an array or a blot), detect the nucleic acid, or quantify the amount of a specific nucleic acid in a sample. In one aspect, message isolated from a cell or a cDNA library are amplified.

The skilled artisan can select and design suitable oligonucleotide amplification primers. Amplification methods are also well known in the art, and include, e.g., polymerase chain reaction, PCR (see, e.g., PCR Protocols, A Guide to Methods and Applications, ed. Innis, Academic Press, N.Y. (1990) and PCR Strategies (1995), ed. Innis, Academic Press, Inc., N.Y., ligase chain reaction (LCR) (see, e.g., Wu (1989) *Genomics* 4:560; Landegren (1988) *Science* 241:1077; Barringer (1990) *Gene* 89:117); transcription amplification (see, e.g., Kwoh (1989) *Proc. Natl. Acad. Sci. USA* 86:1173); and, self-sustained sequence replication (see, e.g., Guatelli (1990) *Proc. Natl. Acad. Sci. USA* 87:1874); Q Beta replicase amplification (see, e.g., Smith (1997) *J. Clin. Microbiol.* 35:1477-1491), automated Q-beta replicase amplification assay (see, e.g., Burg (1996) *Mol. Cell. Probes* 10:257-271) and other RNA polymerase mediated techniques (e.g., NASBA, Cangene, Mississauga, Ontario); see also Berger (1987) *Methods Enzymol.* 152:307-316; Sambrook; Ausubel; U.S. Pat. Nos. 4,683,195 and 4,683,202; and Sooknanan (1995) *Biotechnology* 13:563-564.

vii. Methods of Producing the TIGG Complexes

Typically, the TIGG complexes are made by combining and incubating TGF-beta protein(s) with Ig protein(s) under conditions whereby they associate, typically via non-covalent bonds. Methods for stable, non-covalent binding of certain types of molecules, particularly small molecules, to immunoglobulin (Ig) are well known. For example, a systematic study was undertaken to determine the optimized parameters for chlorambucil binding to rabbit immunoglobulin G (Blakeslee, D. and Kennedy, J. C., Cancer Res. 34:882-885, 1974). Parameters such as temperature, time of reaction, molar concentrations and stoichiometry, ionic strength and pH were analyzed. Researchers found that conditions which favor non-covalent attachment of chlorambucil to IgG include: low ionic strength (down to 0 mM NaCl), high pH (up to 11.5), increased time (up to 30 minute reaction time), and higher temperature of reaction (up to 37° C.). On the other hand, IgG in solution is known to aggregate spontaneously over time, and this aggregation is via the Fc region. A highly alkaline environment disaggregates IgG into monomers, and this may allow otherwise masked binding sites available for binding.

In one embodiment, the methods include combining TGF-beta protein and Ig (e.g. IgG), such as recombinant IgG, under conditions whereby they associate, such as by non-covalent bond. Incubation and binding typically is followed by purification, such as by any well-known protein purification methods including chromatography.

The proteins can be combined under different buffer and temperature conditions and should be combined under conditions whereby the Ig and TGF-beta portions associate via non-covalent bond. Optimal conditions can be determined based on experimentation, for example as described in Example 1. For example, among the buffers for use in combining the TGF-beta and Ig portions are PBS (phosphate buffered saline) and 0.1M Tris pH 7.4. These buffers can further include glycerol, such as 10% glycerol. Also among the suitable buffers are buffers with higher pH values, such as 0.5 M PBS supplemented with NaOH to a pH of 11.

In one particular embodiment, the buffer is a relatively low-hydrophobicity and/or non-polarizing buffer (such as a buffer containing no or little NaCl concentration (e.g. less than at or about 0.15 mM NaCl), e.g. 0.1M Tris pH 7.4.). In one aspect, the buffer does not contain glycerol. In another embodiment, the buffer is an alkaline buffer, such as a buffer with a pH of at least at or about 7, and typically at least at or about 8, 9, 10, 11, or 12, such as PBS (or 0.5×PBS) at a pH of 11. In one aspect, such a buffer is made by diluting PBS with NaOH or other base to a pH of 11, where the buffer contains 0.5×PBS (0.075 mM NaCl). In one example, the TGF-beta protein is suspended in 4 mM HCL, and added to Ig solution in PBS, and the solution diluted in PBS, such as PBS or 0.5×PBS having an alkaline pH, such as a pH of at least at or about 7, and typically at least at or about 8, 9, 10, 11, or 12.

Typical incubation temperatures include room temperature (e.g. at or about 25° C.) and higher temperatures, such as 42° C. The time of incubation (binding) also can vary, and can include 1, 2, 3, 4, 5, 6, 7, 8, 9, 10, 15, 20, 25, 30, or 60 minutes, or 2, 3, 4, 5, 6, 7, 8, 9, 10, 15, 16, 17, 18, 19, 20, 21, 22, 23, or 24 hours or more.

In one example, human TIGG is produced as follows: Total human gamma globulin (available commercially as human "IVIG") is resuspended to a final concentration of 10 mg/ml, for example, in PBS or water. Transforming growth factor-beta is resuspended in 4 mM hydrochloric acid to a final concentration of 100 ng/ml. The TGF-beta solution is added to the IVIG solution at a molar concentration of at least 10:1 IgG to TGF-beta and mixed. To this mixture, an equal volume of PBS (titrated to pH 11 with sodium hydroxide) is added, mixed, and incubated at room temperature for 5 minutes. This solution is then adjusted to pH 7.4 and purified by chromatography.

In one example, the TIGG is purified by adding the TIGG to a column, such as a Sepharose G-50 spin column, or a Superdex 200 HR 10/30 (Vt: 24 ml), 1.0 ml/min (76 cm/h) column, which can be equilibrated with 0.05 M sodium phosphate, 0.15 M NaCl, pH 7.0. The TIGG is purified by polyethylene glycol (PEG) precipitation, such as by incubating with PEG, such as PEG8000 (e.g., 8%), centrifuging and washing the pellet in one or more washes.

The proteins eluting from the column can be monitored to determine binding of the TGF-beta and Ig portions, such as by size determination, for example, using free TGF-beta and/or TIGG complexes as a control. In one example, the presence of protein in the fractions eluted from the column is measured by determining the absorbance of the fractions at 280 nm and/or by analyzing the fractions for TGF-beta presence by ELISA. Such methods are well-known in the art.

Also among the provided complexes and proteins are those containing TGF-beta and IgG portions that are prepared by other known methods for associating two proteins, such as by covalent bonds, and/or using peptide linkers to link the TGF-beta and Ig portions (e.g. by generating nucleic acid vectors encoding the peptide linkers and the proteins), using methods known in the art, such as methods for making fusion proteins containing an Ig and a TGF-beta portion.

viii. Methods for Evaluating the TGF-Beta Containing Complexes

As noted, in one embodiment, the TIGGs are used to target cells with functional FcγRs. Thus, the TIGGs (and portions thereof) typically are defined in part by functional properties, such as their ability to bind and target particular cell types, e.g. by binding to particular FcγRs, and their TGF-beta activity.

Methods are provided for evaluating properties of the provided proteins and complexes, e.g. the TIGGs and portions thereof. The methods include evaluation of properties, e.g. binding affinities and activity, in vitro, and in vivo methods to assess targeting of cell types and in vivo effects of the TIGGs.

a. Binding Affinities

Binding affinity of the TIGG and portions thereof for other molecules, typically for Fc receptors and/or TGF-beta receptors can be specified, and can be determined using well-known methods. The affinity can be measured using well-known methods and expressed using well-known units of affinity (e.g. $K_a$, $K_d$, $K_D$). Typically, the affinity is specified by expressing a ratio or percentage of the affinity of the TIGG for the molecule, compared to the affinity of another Ig protein or complex for that molecule (e.g. for a particular Fc receptor).

Affinities of proteins or complexes (e.g. Ig proteins) for Fc receptors can be determined using well-known experimental techniques, such as those described, for example, by: Nimmerjahn and Ravetch (Science, 310:1510-1512, 2005); Nimmerjahn et al. (Immunity, 23: 41-51 (2005); and Armour, K L et al., Mol Immunol, 40:585-593, 2003. For example, affinities ($K_A$) of proteins or complexes for FcγRs can be measured by a variety of kinetic and thermodynamic assays, including optical detection as BIAcore and RIfS, equilibrium titration and stopped-flow fluorescence. In one aspect, binding affinities are determined using the assays set out in the examples. In one aspect, the affinities are determined by surface plasmon resonance as described by Nimmerjahn and Ravetch (Science, 310:1510-1512, 2005) (see supplemental online materials). Briefly, a Biacore sensor system is used to assay the interaction of soluble FcγRs with the proteins by immobilizing the proteins at high and low densities to flow cells of CM5 sensor chips (Biacore) by standard amine coupling. Soluble Fcγ-receptors are injected at different concentrations through flow cells at room temperature in HBS-EP running buffer (10 mM Hepes, pH 7.4, 150 mM NaCl, 3.4 mM EDTA, and 0.005% surfactant P20) at a flow rate of 30 µl/min. Soluble Fc-receptors are injected for 3 minutes and dissociation of bound molecules is observed for 10 minutes. Background binding to control flow cells is subtracted automatically. Control experiments can be performed to exclude mass transport limitations. Affinity constants are derived from sensorgram data using simultaneous fitting to the association and dissociation phases and global fitting to all curves in the set. Alternatively, soluble Fc-receptors can be immobilized to sensor chips. Affinities can also be measured by flow cytometry, for example, as described by Armour, K L et al., Mol Immunol, 40:585-593, 2003, and by other known techniques for measuring binding affinities of proteins. Affinities can be measured for any of the Fc receptors and variants of Fc receptors.

b. Activity

Also provided are methods for evaluating other properties of the complexes and proteins, e.g. the TIGGs and proteins thereof, such as measuring activities and in vitro and in vivo effects. For example, the TGF-beta activity of a TIGG, or TGF-beta portion or protein thereof, can be measured using a number of well-known techniques, including in vivo and in vitro assays, such as soft agar assays, ability to inhibit proliferation, survival, growth and/or differentiation of a TGF-beta receptor-expressing cells and/or cells known to be inhibited by TGF-beta (in vivo or in vitro), and radioreceptor assays and assays for measuring the production of various cytokines and/or chemokines by cells incubated with the TIGG (for example, as compared to cells incubated with wild-type TGF-beta). Assays for measuring activity further include assays for assessing the ability of a TIGG or portion to target a particular cell type and/or to treat a disease or condition and/or associated symptom.

In one embodiment, the TIGGs and/or portions thereof are evaluated by incubating the complexes in vitro with one or more cell types, or administering the TIGGs to a subject, e.g. non-human animal or human. While FcγR are expressed in most immune cell types, assay of the efficacy of the TIGGs can be assessed by evaluating specific cell types and/or readouts of the functions of such cell types. In one example, a TIGG that alters this ratio is most effectively assayed by evaluating the expression pattern of monocytes, such as macrophages. In one aspect, the macrophages are isolated from animals treated by the test material. In another aspect, the monocytes are assayed following treatment with the product in vitro.

For example, provided are methods for evaluating TIGG, when incubated with purified or enriched macrophages before being activated with *E. coli* LPS, will alter the expression pattern of the cultured macrophages. In one aspect, the TIGG-treated macrophages will produce 5%, 10%, 15%, 20%, 25% or less of IL-1beta protein in culture compared to untreated, similarly cultured and activated macrophages.

Also provided are methods for evaluating the in vivo effects of the complexes, e.g. the TIGGs. For example, to evaluate whether a TIGG will ameliorate osteoarthritis in vivo, a canine model of osteoarthritis can be used.

C. Therapeutic Applications

Provided are methods for using the TGF-beta containing complexes, such as TIGG. Also provided are methods and uses for administration of a therapeutic composition comprising TIGGs to an individual diagnosed with osteoarthritis and/or a degenerative joint disease.

For example, provided are methods for modulating cellular activity (e.g. affecting cell growth, proliferation, survival and/or differentiation) using the provided TIGGs. Among the provided methods are methods for administering the TIGGs to subjects, such as non-human animals and humans, for example for treatment, prevention or amelioration of a disease or condition, such as diseases and conditions associated with osteoarthritis. Typically, the TGF-beta-containing complexes are activated by particular cells. In one aspect, the cells which activate TIGG are immune cells, such as type A cells within the synovial lining, which have properties that are macrophage-like, including possessing functional FcγRs.

The provided TIGG complexes and compositions containing the TIGGs overcome problems and limitations associated with free TGF beta administration, e.g. administration (e.g. injection) of TGF-beta not associated with Ig portions. For example, active TGF-beta can have a short in vivo half-life (2-3 minutes in rats and rabbits) when injected i.v., and can have pleiotropic activity (on a plurality of cells and tissues, such as throughout the body). Pleiotropic activity can have problematic effects, for example, by acting on tissues and/or cell types where activity is not desired.

The provided complexes overcome these limitations. For example, among the provided complexes are those having increased half-lives, compared to TGF-beta not associated with Ig molecules. For example, provided are complexes having half-lives greater than at or about 2 minutes, 3 minutes, 4 minutes, 5 minutes, 1 hour, 2 hours, 3 hours, 5 hours, 10 hours or 24 hours, and having TGF-beta activity, such as substantially the same TGF-beta activity, or greater, compared to wild-type active TGF-beta. Further, the complexes and compositions are activated by immune cells specifically, such as cells expressing Fc receptors (e.g. Fc gamma receptors), and in particular macrophage-like cells that are contained within the synovial lining of the joint i. Methods of Using TIGGs Provided are methods for using the TIGGs. For example, administration of the provided TIGG protein can be either for preventative or therapeutic purpose. When provided preventatively, the therapeutic agent is provided in advance of any symptoms. The preventative administration of the therapeutic agent serves to prevent or attenuate any symptoms. When provided therapeutically the therapeutic agent is provided at (or shortly after) the onset of a symptom of osteoarthritis. The therapeutic administration of the therapeutic agent serves to attenuate any actual exacerbation of the symptoms. The individual treated may be any mammal. In one aspect, the mammal is a human. In another aspect, the mammal is a dog. In another aspect, the mammal is a cat. In another aspect, the mammal is a horse.

The subject treated by the present methods includes a subject having an osteoarthritic joint susceptible to treatment. Such osteoarthritic joints can involve the knee, hip, spine, elbow, wrist, finger, ankle, shoulder, or tempomandibular joints in humans. Such osteoarthritic joints can involve the hip, knee (hock), elbow, or shoulder joints or joints in the spine of dogs, horses or cats.

D. Pharmaceutical Compositions, Dosing and Administration

Various routes of administration and dosing regimens can be used for administering a therapeutically effective amount of TIGG to a human. The provided therapeutic composition can be administered by any of the conventional routes of administration. Also, the therapeutic composition can be in any of several conventional dosage forms. In one aspect, the therapeutic composition is administered by intra-articular injection. In another aspect, the therapeutic composition is administered by intra-articular injection after arthrocentesis.

The TIGG may be administered subcutaneously, transdermally, orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, or intrathecally. The TIGG may also be administered or co-administered in slow release dosage forms.

The dose at which the TIGG may be administered to a human or animal may vary, depending on the particular route of administration and the disease state.

For example, the TIGG may be administered at a dose of at least 0.0001 mg, optionally at least 0.001 mg, optionally at least 0.01 mg, optionally at least 0.05 mg, optionally at least 0.1 mg, optionally at least 0.5 mg, or optionally at least 1 mg. In other embodiments, the TIGG may be administered at a dose of 0.01-1000 mg, optionally at a dose of 0.1-500 mg, optionally at a dose of 1-200 mg, optionally at a dose of 1-100 mg, optionally at a dose of 1-50 mg, optionally at a dose of 1-20 mg, optionally at a dose of 0.1-5 mg, or optionally at a dose of about 1-5 mg.

In still further embodiments, the TIGG may be administered to a mammal at a dose calculated based on the suffer area of the treated mammal, e.g., at dose of 0.01-1000 mg/m$^2$, optionally at dose of 0.1-500 mg/m$^2$, optionally at dose of 1-200 mg/m$^2$, optionally at dose of 1-100 mg/m$^2$, optionally at dose of 1-50 mg/m$^2$, optionally at dose of 1-20 mg/m$^2$, optionally at dose of 0.1-5 mg/m$^2$, or optionally at dose of 1-5 mg/m$^2$.

The treatment cycle for TIGG may be administered once, or more than once. For example, it can be administered weekly, biweekly, monthly, or on an as-needed basis. In other aspects, it is administered once, twice per day or more times per day. The treatment may be given in conjunction with other therapeutic agents or before or after surgery.

Various pharmaceutical compositions and techniques for their preparation and use will be known to those of skill in the art in light of the present disclosure. For a detailed listing of suitable pharmacological compositions and associated administrative techniques one may refer to the detailed teachings herein, which may be further supplemented by texts such as REMINGTON: THE SCIENCE AND PRACTICE OF PHARMACY 20th Ed. (Lippincott, Williams & Wilkins 2003).

It is further understood that the provided polypeptides may be used in the form of pharmaceutically acceptable salts, and that any reference herein to pharmaceutical compositions comprising the polypeptides also refers to said salts. Pharmaceutically-acceptable materials, composition or vehicle, such as a liquid or solid filler, diluent, excipient, solvent or encapsulating material, involved in carrying or transporting the subject chemical from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Combinations and articles of manufacture, such as kits, comprising the compositions are also provided.

Animal Models of Osteoarthritis

Chemically- or enzymatically-induced osteoarthritis are well-known and widely used animal models of osteoarthritis in mice and rats. For example, male C57Bl mice, 10 weeks of age, can be induced to display clinical signs of osteoarthritis by injection directly into the joint capsule. Mice are injected directly into the right knee joint, directly through the patellar ligament, with 6 microliters of active solution. The active solution can contain: sodium iodoacetate at a concentration of 0.1%, 0.5% or 1% (w/v); collagenase (Clostridial, 248 units/mg, Worthington Biochemical Corporation, Freehold, N.J.) was injected in the following concentrations: 0.5%, 1.0%, and 1.5% (w/v); or papain (type IV, double crystallized, 15 units/mg, Sigma Chemical Co., St. Louis, Mo.) was used in a concentration of 0.5%, 1.0%, and 2.0% (w/v), and these solutions were supplemented with 0.03 M L-cysteine HCl (Sigma) to activate the papain. Controls for each of these models are the injection of 6 microliters of phosphate-buffered saline into the left knee joint.

For histological assessment of arthritis, groups of five mice injected with papain or collagenase are killed by cervical dislocation 1, 3, 7, 21, and 42 days after intra-articular injection, whereas an additional group of mice injected with iodoacetate are also killed after 64 days. Carefully dissected knee joints are fixed in phosphate-buffered formalin (pH 7.4) for 5 days and subsequently decalcified in 5% formic acid for 4 days. Standard processing of the knee joints in an automatic tissue processing apparatus is followed by embedding of the knee joints in paraffin wax. Frontal whole knee joint sections are prepared (6, um) and stained with safranin 0 and fast green.

Soft tissue joint swelling after intra-articular injection can be assayed on day 1, 3, 7, 21, 41, and 64 (iodoacetate) by the $^{99}$Tc-pertechnetate uptake method. In short, mice are injected with 15 $\mu Ci^{99}mTc$ and sedated with choral hydrate (intraperitoneally). After 30 minutes, the quantity of radiolabel in the right and left knee joints is determined by measuring the gamma radiation with a collimated NaI-scintillation crystal while the knee joint is in a fixed position. Joint swelling is scored as the ratio of the radiolabel in the right and the left knee joint.

To determine glycosoaminoglycan synthesis after 1, 3, 7, 21, 42, and 64 (iodoacetate) days, groups of five mice are killed and the whole patellae, along with a standard amount of surrounding tissue, are dissected from both the left and the right knee joints. Patellae are incubated in RPMI 1640 DM medium (Flow Laboratories, Irvine, UK) containing 20 ACi [35S]sulfate (1200 Ci/mmol, Radiochemical Centre Amersham, Amersham, UK) for 2 hours at 37° C. in a humidified 5% CO2 atmosphere. After incubation the patellae are washed twice with physiologic saline to remove nonincorporated label and fixed in 4% phosphate-buffered formalin (pH 7.4). The patellae are isolated from the surrounding tissue after overnight decalcification in 5% formic acid. The patellae are digested with Lumasolve (Hicol, Oud-Beijerland, The Netherlands), and the incorporated radiolabel is determined by liquid scintillation counting.

The ability of TIGG to ameliorate osteoarthritis can be tested in these models, e.g. after initial signs of the disease appear.

E. Examples

Example 1

Production of TIGGs

This example describes production of TIGG using both mouse and rat IgG.

A. Optimization TGF-Beta Binding to IgG

This example describes the optimization of conditions for generating the TIGG. 10 μL 1 mg/mL rat total IgG (Sigma-Aldrich St. Louis, Mo.) first was bound to Nunc Immunosorb plates in 0.1M NaCO$_3$, pH 9.6 overnight at 4° C. The plates were washed with TBST and blocked with 3.5% BSA in TBST for 2 hrs at 37° C. Four different samples containing TGF-beta (Leinco Technologies, St. Louis, Mo.; 10 ng per 100 μl volume) then were prepared, to evaluate the binding of TGF-beta to IgG with and without salt and with and without glycerol. A control sample also was prepared, containing no TGF-beta.

Accordingly, 100 μL volumes of each of the following five samples was added to a well of the blocked ELISA plate: (1) PBS alone (no TGF-beta—negative control); (2) 0.1M Tris pH 7.4 (0 mM NaCl); (3) PBS (0.15 mM NaCl); (4) 10% glycerol in 0.1M Tris pH 7.4 (decreased hydrophobicity (0 mM NaCl)); and (5) 10% glycerol in PBS (increased hydrophobicity (0.15 mM NaCl). The samples were incubated on the plates for 18 hours at 4° C. After washing with TBST, the remaining TGF-beta (bound to IgG) was assayed using eBioscience Human/Mouse TGF-1 ELISA Ready-Set-Go! Kit (EBioscience). Resulting net absorbance units are listed in Table 2, below.

TABLE 2

Binding of TGF-beta to total IgG under varying conditions

| Sample | Binding condition | Net Absorbance (450) |
|---|---|---|
| 1 | Negative control (no TGF-beta added - PBS alone): | 0 |
| 2 | TGF-beta/Tris: | 1.02 |
| 3 | TGF-beta/PBS | 0.18 |
| 4 | TGF-beta/Tris/Glycerol | 0.70 |
| 5 | TGF-beta/PBS/Glycerol | 0 |

The results, shown in Table 2, revealed that binding of TGF-beta to IgG was improved in a low-salt environment (Tris, 0 M NaCl) compared to a polarizing environment (PBS, 0.15 mM NaCl). The presence of glycerol decreased binding in both environments.

Following the study described above, additional optimization studies were carried out to evaluate binding of TGF-beta to soluble IgG at different salt concentrations, pHs, and temperatures. For these studies, TGF-beta (Peprotech, Rocky Hill, N.J.) was diluted to 20 µg/mL in PBS and total mouse IgG (Sigma-Aldrich) was diluted to 1 mg/mL in PBS. The diluted TGF-beta and IgG were combined, and incubated for five minutes, with the following buffer and temperature conditions (Table 3) for samples 1-4:

TABLE 3

Combining TGF-beta and IgG

| | Sample 1 (TGF-β only control) | Sample 2 | Sample 3 | Sample 4 |
|---|---|---|---|---|
| TGF-beta | 20 ng | 20 ng | 20 ng | 20 ng |
| IgG | 0 (1 µL PBS) | 1 µg | 1 µg | 1 µg |
| Equal volume (2 µL) buffer | PBS | PBS | PBS | 0.5 × PBS (0.075 mM NaCl)w/ NaOH to pH 11 |
| Incubation at temperature | RT | RT | 42° C. | RT |

*** RT = room temperature (approximately 25° C.)

After incubation for five minutes, a 2× volume (4 µL) of 1 M Tris, pH 8 was added to each sample in Table 3. Each sample then was added to a Sepharose G-50 spin column that had been equilibrated with 1% BSA in PBS (to prevent nonspecific binding). Bound material was eluted from the column and the presence of TGF-beta in the eluates evaluated by ELISA. For the ELISA, the eluates were bound to a 96 well plate in NaCO$_3$, pH 9.6, for 2 hours at 37° C. Following washes with TBST, the plates were blocked as described above. An anti-TGF-beta antibody then was added, followed by washing with TBST and developing using the eBioscience kit referenced above. Table 4, below, sets forth the resulting net absorbance units.

TABLE 4

Net absorbance values (TGF-beta ELISA from binding study of Table 3)

| Sample | Binding condition | Net Absorbance (450) |
|---|---|---|
| 1 | TGF-beta only control, RT | 0 |
| 2 | PBS, RT | 0.1926 |
| 3 | PBS 42° C. | 0.1166 |
| 4 | 0.5 × PBS pH 11, RT | 0.5585 |

B. Production of TIGG

Based on the optimization studies in Example 1A, two different mouse TIGGs were produced. Transforming growth factor-beta 1 was purchased from Peprotech (Rock Hill, N.J.) as a lyophilized solid. Mouse IgG1 and Mouse IgG2a were purchased as 1 mg/ml solutions in PBS from eBioscience (San Diego, Calif.). Just before use, TGF-beta was resuspended in 4 mM HCl to a final concentration of 50 µg/ml. For production of TIGG, the TGF-beta solution was then added to separate IgG1 and IgG2a solutions at a molar ratio of 1:10 TGF-beta to IgG, at room temperature. After 5 minutes, the solution was diluted to a final concentration of 500 ng/ml TGF-beta in PBS and the pH adjusted to 7.4. The solution was incubated at 4° C. for 18 hrs.

For analysis of the TIGGs TGF-beta-bound mIgG1 and mIgG2a were run over a Sephadex G-50 column (⅙₀th column volume), by gravity flow, that had been equilibrated in PBS/1% BSA. Fractions were analyzed by ELISA, as described in Example 1A above, to assess the presence of TGF-beta. The results revealed that approximately 40-50% of TGF-beta eluted as a broad peak just after the void volume, representing the IgG-bound TGF-beta fraction. The remaining TGF-beta eluted in a broad peak just before the total column volume, representing unbound TGF-beta.

Example 2

Production of Human TIGG

In one example, human TIGG is produced as follows: Total human gamma globulin (available commercially as human "IVIG") is resuspended to a final concentration of 10 mg/ml, for example, in PBS or water. Transforming growth factor-beta is resuspended in 4 mM hydrochloric acid to a final concentration of 100 ng/ml. The TGF-beta solution is added to the IVIG solution at a molar concentration of at least 10:1 IgG to TGF-beta and mixed. To this mixture, an equal volume of PBS (titrated to pH 11 with sodium hydroxide) is added, mixed, and incubated at room temperature for 5 minutes. This solution is then adjusted to pH 7.4 and purified by chromatography.

In one example, human TIGG is produced as follows: Human IgG4 is resuspended to a final concentration of 10 mg/ml, for example, in PBS or water. Transforming growth factor-beta is resuspended in 4 mM hydrochloric acid to a final concentration of 100 ng/ml. The TGF-beta solution is added to the IgG4 solution at a molar concentration of at least 10:1 IgG to TGF-beta and mixed. To this mixture, an equal volume of PBS (titrated to pH 11 with sodium hydroxide) is added, mixed, and incubated at room temperature for 5 minutes. This solution is then adjusted to pH 7.4 and purified by chromatography.

Example 3

Purification of TIGG

For purification of the mouse TIGG produced in example, 1B, one-third volume of 32% PEG (MW 8000) in water or PBS was added to the neutralized TIGG reaction mixture (following adjustment to pH 7.4 in Example 1B), giving a final concentration of 8% PEG. The mixture was incubated for 1 hour at 4° C., centrifuged at 12 kg for 30 minutes, and the supernatant discarded. The pellet was washed with cold (4° C.) 8% PEG, centrifuged an additional 10 minutes at the same speed, and the pellet retained.

For purification of human and/or mouse TIGG (e.g., as produced in Example 1 or 2 (1 ml, less than 15 mg/ml)), the TIGG is added to a Superdex 200 HR 10/30 (Vt: 24 ml), 1.0 ml/min (76 cm/h) equilibrated with 0.05 M sodium phosphate, 0.15 M NaCl, pH 7.0. Absorbance is monitored at 280 nm and fractions assayed for TGF-beta by Elisa. The first peak after the void volume is collected and retained.

Example 4

Assessing the Purity and Integrity of TIGG

An apoptosis assay, using mink lung epithelial cells (ATCC® Number CCL-64), was performed to assess the purity and integrity of the samples containing purified mouse TIGG, produced in Example 3. For this assay, CCL-64 cells, grown in minimal essential media supplemented with 5% fetal bovine serum were aliquoted into 96-well tissue culture wells at about $1 \times 10^4$ cells per well and allowed to acclimate at 37° C., 5% $CO_2$ overnight.

Before incubation with these cells, the purified TIGG from Example 3 was resuspended in PBS, and divided into two aliquots. One aliquot ("Intact") was analyzed as is. The other aliquot ("Treated") was first incubated with acid to dissociate the TIGG into free TGF-beta and immunoglobulin, by adding 1N HCl (1:25 final volume) and incubating at room temperature for 30 minutes, followed by neutralization with 1N NaOH.

The Intact and Treated samples then were analyzed by incubation with the cells in the same procedure as follows. Samples were added to CCL-64 cells at various concentrations in triplicate and incubated for 24 hours in a humidified 5% $CO_2$ incubator at 37° C. Cells in "Control" wells were incubated under the same conditions with PBS alone. The In Vitro Toxicology Assay Kit, XTT based (Sigma Aldrich, St. Louis, Mo.), was utilized to monitor cell viability according to the manufacturer's instructions. Briefly, the XTT stock solution was reconstituted and added to each well at an amount equal to 20% of the culture medium volume. The cultures were incubated at 37° C. for an additional 4 hours with occasional gentle mixing. Absorbance was measured at 450 nm, with 690 nm as background absorbance.

The results are presented in Table 5, below. The table lists cell viability ($OD_{450}$ relative to $OD_{450}$ in Control wells (cells incubated with PBS alone)) vs. TIGG concentration (pg/ml) for each sample. The results show higher viability of cells incubated with Intact samples, compared to "Treated" wells, indicating that the TIGG prepared in Example 3 was relatively devoid of free TGF-beta, contained intact TIGG complex (which did not binding the TGF-beta receptors on the cells), and was dissociated into free TGF-beta and immunoglobulin upon treatment with acid (Treated samples); these data confirm the purity and integrity of the TIGG preparation.

TABLE 5

Intact and Acid-Dissociated (Treated) TIGG Treatment of Mink Lung Epithelial Cells, Monitored for Cell Viability

| TIGG Concentration | Cell Viability ($OD_{450}$/Control $OD_{450}$) | |
| --- | --- | --- |
| (pg/mL) | Intact TIGG | Dissociated (Treated) TIGG |
| 0 | 1 | 1 |
| 0.25 | 0.965 | 0.621 |
| 2.5 | 0.924 | 0.645 |
| 25 | 0.897 | 0.651 |
| 250 | 0.817 | 0.651 |
| 2500 | 0.678 | 0.616 |

Example 5

Activating TIGG in Mouse Macrophages in Cell Culture

In order to assess activation of TIGG in macrophages in cell culture, peritoneal cells are obtained by peritoneal lavage of untreated mice. The macrophages are enriched using MS columns on MiniMACS Separator (Miltenyi Biotec) by depletion with anti-CD19 and anti-CD5 microbeads (Miltenyi Biotec) per the manufacturer's instructions. The resulting cell populations are >95% CD5−, CD19−, and CD11b+. The cells are resuspended in RPMI 1640 with 5% FBS, dispensed to standard 24- or 48-well cell culture plates with the TIGG, or PBS control for 24 hours, followed by activation by 24 h culture with 0.1 mg/ml LPS (*Escherichia coli* 011B, Sigma-Aldrich, St. Louis, Mo.).

After activation, the cell culture media are assayed for the levels of TGF-beta activity. Assays are performed as explained in Example 4.

Example 6

Activating TIGG in Human Macrophages in Cell Culture

In order to assess activation of TIGG on human macrophages in cell culture, human monocyte-derived macrophages are isolated and cultured using standard techniques ("Basic Cell Culture Protocols," Helgason, C D and Miller, C L, Methods in Molecular Biology, Volume 290, Humana Press, 2005).

The cells are resuspended in RPMI 1640 with 5% FBS, dispensed to standard 24- or 48-well cell culture plates with TIGG, or PBS control for 24 hours.

After activation, the cell culture media are assayed for the levels of TGF-beta activity. Assays are performed as explained in Example 4.

Example 7

Assessing the Effect of Activated TIGG on Macrophage Interleukin-1 Beta Production in Culture In order to evaluate the in vitro effects of activated TIGG on the production by macrophages of interleukin-1 beta, macrophages are first isolated from mice. BALB/c mice, about 7 weeks of age are injected intraperitoneally with 3 ml of thioglycolate medium (Difco Laboratories, Detroit, Mich.). Peritoneal macrophages are prepared from the mouse peritoneal exudates cells as described (Hanazawa, S., et al., Infect. Immun. 59:197201977 (1991)). Macrophage monolayers are prepared by culturing the cells ($5 \times 10^6$) in RPMI 1640 with 5% fetal calf serum in Falcon 9-cm-diameter plastic plates. Individual cultures are treated overnight with various quantities of activated TIGG, as obtained in Example 3. The next day, samples are treated with 100 ng/ml LPS. The following day, interleukin-1 beta is measured in the culture media by ELISA using anti-mouse IL-1 beta antibody (BioSource International, Inc., Camarillo, Calif.

Example 8

Assessing the Effect of Activated TIGG on Chondrocyte Nitric Oxide Production in Culture To evaluate the in vitro effects of activated TIGG on the production by immortalized chondrocytes, a murine H4 chondrocyte cell line (van Beuningen H M, et al., Osteoarthritis Cartilage 10:977-986 (2002)) are cultured at 37° C. in humidified 5% carbon dioxide atmosphere in Dulbecco's modified Eagle's medium and Ham's F12 medium both with L-glutamine (1:1, v:v). Culture medium is supplemented with 10% heat-inactivated fetal bovine serum, penicillin (100 units/ml), streptomycin (100 micrograms/ml) and amphotericin B (250 ng/ml). Cells are seeded on 24-well plates and grown to confluence for 24 hours.

Dose-dependent inhibitory effect of activated TIGG on IL-1 beta-induced nitric oxide production are determined using activated TIGG from Example 3. Chondrocytes are incubated with IL-1 beta (R&D Systems, Inc., Minneapolis, Minn.) and increasing concentrations of activated TIGG. Concentrations of nitrate, a stable product of NO in aqueous solutions, are then measured in the culture medium using the Griess reaction (Green, L C, et al., Anal Biochem. 126:131-138 (1982)) and using sodium nitrate as a standard.

Example 9

Assessing the Effect of TIGG on Interleukin-1 Beta-Induced Destruction of Articular Cartilage In Vivo To evaluate ability of TIGG to diminish IL-1 beta-induced destruction of articular cartilage in vivo, C57B1/10 mice are used as an animal model. Mice are pretreated 24 hours before test injections by prelabelling articular cartilage with 74 kBq [$^{35}$S]sulphate/g body weight, injected subcutaneously. Increasing concentrations of intact TIGG are injected (6 microliters for each injection) into the joint space of the right knee, with the left knee receiving an equal volume injection of PBS as a control. One hour after the injections, 30 units of IL-1 beta (R&D Systems, Inc., Minneapolis, Minn.) are injected into the right knee and an equal volume of PBS is injected into the left knee. After 24 hours, animals are sacrificed and patellae from left and right knees are analyzed for $^{35}$S concentrations to determine proteoglycan synthesis/retention.

Example 10

Assessing the Effect of TIGG on Amelioration of Disease in Dogs with Osteoarthritis To evaluate the ability of TIGG to diminish pain, lameness and cartilage destruction in dogs with osteoarthritis, dogs with naturally occurring osteoarthritis are treated with TIGG by intra-articular injection following arthrocentesis. Dogs to be treated with TIGG are male or female, between 1 and 11 years of age, and have been diagnosed with coxofemoral (hip), stifle (knee) or elbow osteoarthritis with a minimum duration of 6 months. Dogs with concomitant NSAID therapy are required to be on these treatments for at least 14 days prior to treatment and remain on the drugs at the same levels throughout the study. Exclusion criteria include a history of joint surgery in the affected joint, very severe hip dysplasia with functional luxation, a history or high likelihood of spontaneous luxation, and concurrent disease such as viral, bacterial or fungal infection, cancer, or any severe systemic disease that would confound interpretation of the treatment effects.

Dogs are assessed before treatment, and after treatment. Assessment can include radiographic assessment, and physical assessment.

Each dog in the study is given a pretreatment radiographic assessment of evidence of osteoarthritis and will have a grade of 2 or above in the following scale:
   0—Normal
   1—Radiographically demonstrated instability with no degenerative change
   2—Radiographically demonstrated mild degenerative change
   3—Radiographically demonstrated moderate degenerative change with subchondral sclerosis
   4—Radiographically demonstrated severe degenerative change with subchondral sclerosis and bone remodeling
   These same criteria are assessed at 1 month, 3 months and 6 months after treatment.

To evaluate the effect treatment with TIGG has on pain and function, the treating veterinarian will assess the dogs using the following criteria:
Lameness:
1. Walk normally
2. Slightly lame when walking
3. Moderately lame when walking
4. Severely lame when walking
5. Reluctant to rise and will not walk more than 5 paces
Weight Bearing:
1. Equal on all limbs
2. Normal standing, favors affected limb when walking
3. Partial weight-bearing, standing and walking
4. Partial weight-bearing standing, non-weight-bearing walking
5. Non-weight-bearing standing and walking
Pain on Palpitation
1. No pain detectable
2. Mild signs; dog turns head in recognition
3. Moderate signs; dog pulls limb away
4. Severe signs; dog vocalizes or becomes aggressive
5. Dog will not allow palpitation
Joint Mobility
1. Full range of motion
2. Mild limitation (10-20%), no crepitus
3. Mild limitation (10-20%), crepitus
4. Moderate limitation (20-50%), with or without crepitus
5. Severe limitation (>50%), with or without crepitus
Overall Score of Clinical Condition:
1. Not affected
2. Mildly affected
3. Moderately affected
4. Severely affected
5. Very severely affected
Dogs are rated using one or more of these criteria before treatment begins, at day 21 and at day 90.

Veterinary professionals treating and assessing the dogs in this study are blinded with respect to treatment of the dog with TIGG or PBS as a control. For treatment, dogs are anesthetized (local or general) and the joint to be treated is prepared for injection. A 20 gauge needle attached to a 5 ml syringe is inserted into the affected synovium and as much fluid as possible is withdrawn. The syringe barrel is detached and a new syringe containing TIGG (50 nanograms/ml) or PBS is attached to the inserted needle. The volume initially withdrawn is replaced with treatment solution. The syringe needle is withdrawn and the injection site is dressed.

The administration of one or more TIGGs in this animal model improve one or more of these test criteria, and are thus useful for the treatment of osteoarthritis.

The invention claimed is:

1. A method for promoting cartilage growth in a subject having osteoarthritis or degenerative joint disease, comprising administering a therapeutically effective amount of a pharmaceutical composition comprising a Transforming Growth Factor-beta-bound IgG (TIGG) to the subject,
wherein the TIGG comprises an immunoglobulin (Ig) portion and a transforming growth factor-beta (TGF-beta) portion,
wherein the TGF-beta portion contains a TGF-beta protein having at least 95% sequence identity to the sequence of amino acids set forth in SEQ ID NO: 1, and the TGF-beta portion binds to a TGF-beta type II receptor (TGF-beta RII);
the Ig portion contains an Ig protein with an Fc region having at least 95% sequence identity to the sequence of amino acids set forth in SEQ ID NO: 2, SEQ ID NO: 3, SEQ ID NO: 4, or SEQ ID NO: 5, and the Ig portion binds to an Fc gamma receptor (FcγR); and
the Ig protein and TGF-beta protein are associated via a non-covalent bond between the constant region of the Ig protein and the TGF-beta protein.

2. The method of claim 1, wherein the Ig portion contains a mammalian IgG or Fc portion thereof.

3. The method of claim 1, wherein the TGF-beta protein, when not associated with the Ig protein in the TIGG, has TGF-beta activity at a physiological pH.

4. The method of claim 3, wherein the TGF-beta activity is at least substantially the same as the TGF-beta activity of a wild-type TGF-beta.

5. The method of claim 3, wherein the TGF-beta activity is at least substantially the same as the TGF-beta activity of a TGF-beta protein having the amino acid sequence set forth in SEQ ID NO: 1.

6. The method of claim 1, wherein the non-covalent bond is between the TGF-beta protein and the Fc region of the Ig protein.

7. The method of claim 1, wherein the administration is an intra-articular injection.

8. The method of claim 1, wherein the subject is a human, a dog, a cat, or a horse.

* * * * *

SEQUENCE LISTING

```
<160> NUMBER OF SEQ ID NOS: 5

<210> SEQ ID NO 1
<211> LENGTH: 112
<212> TYPE: PRT
<213> ORGANISM: Homo sapiens
<220> FEATURE:
<221> NAME/KEY: misc_feature
<222> LOCATION: (1)...(112)
<223> OTHER INFORMATION: coding sequence of human TGF-beta 1

<400> SEQUENCE: 1

Ala Leu Asp Thr Asn Tyr Cys Phe Ser Ser Thr Glu Lys Asn Cys Cys
 1               5                  10                  15

Val Arg Gln Leu Tyr Ile Asp Phe Arg Lys Asp Leu Gly Trp Lys Trp
            20                  25                  30

Ile His Glu Pro Lys Gly Tyr His Ala Asn Phe Cys Leu Gly Pro Cys
        35                  40                  45

Pro Tyr Ile Trp Ser Leu Asp Thr Gln Tyr Ser Lys Val Leu Ala Leu
    50                  55                  60

Tyr Asn Gln His Asn Pro Gly Ala Ser Ala Ala Pro Cys Cys Val Pro
65                  70                  75                  80

Gln Ala Leu Glu Pro Leu Pro Ile Val Tyr Tyr Val Gly Arg Lys Pro
                85                  90                  95

Lys Val Glu Gln Leu Ser Asn Met Ile Val Arg Ser Cys Lys Cys Ser
            100                 105                 110

<210> SEQ ID NO 2
<211> LENGTH: 206
<212> TYPE: PRT
<213> ORGANISM: Homo sapiens
<220> FEATURE:
<221> NAME/KEY: misc_feature
<222> LOCATION: (1)...(206)
<223> OTHER INFORMATION: immunoglobulin IgG1 Fc region GenBank
      AAC82527.1

<400> SEQUENCE: 2

Leu Phe Pro Pro Lys Pro Lys Asp Thr Leu Met Ile Ser Arg Thr Pro
 1               5                  10                  15

Glu Val Thr Cys Val Val Val Asp Val Ser His Glu Asp Pro Glu Val
            20                  25                  30

Lys Phe Asn Trp Tyr Val Asp Gly Val Glu Val His Asn Ala Lys Thr
        35                  40                  45

Lys Pro Arg Glu Glu Gln Tyr Asn Ser Thr Tyr Arg Val Val Ser Val
    50                  55                  60

Leu Thr Val Leu His Gln Asp Trp Leu Asn Gly Lys Glu Tyr Lys Cys
65                  70                  75                  80

Lys Val Ser Asn Lys Ala Leu Pro Ala Pro Ile Glu Lys Thr Ile Ser
                85                  90                  95

Lys Ala Lys Gly Gln Pro Arg Glu Pro Gln Val Tyr Thr Leu Pro Pro
            100                 105                 110
```

```
Ser Arg Asp Glu Leu Thr Lys Asn Gln Val Ser Leu Thr Cys Leu Val
            115                 120                 125

Lys Gly Phe Tyr Pro Ser Asp Ile Ala Val Glu Trp Glu Ser Asn Gly
    130                 135                 140

Gln Pro Glu Asn Asn Tyr Lys Thr Thr Pro Pro Val Leu Asp Ser Asp
145                 150                 155                 160

Gly Ser Phe Phe Leu Tyr Ser Lys Leu Thr Val Asp Lys Ser Arg Trp
                165                 170                 175

Gln Gln Gly Asn Val Phe Ser Cys Ser Val Met His Glu Ala Leu His
            180                 185                 190

Asn His Tyr Thr Gln Lys Ser Leu Ser Leu Ser Pro Gly Lys
            195                 200                 205

<210> SEQ ID NO 3
<211> LENGTH: 210
<212> TYPE: PRT
<213> ORGANISM: Canis familiaris
<220> FEATURE:
<221> NAME/KEY: misc_feature
<222> LOCATION: (1)...(210)
<223> OTHER INFORMATION: immunoglobulin IgG1 Fc region GenBank
      AF354264.1

<400> SEQUENCE: 3

Leu Ile Phe Pro Pro Lys Pro Lys Asp Ile Leu Arg Ile Thr Arg Thr
1               5                   10                  15

Pro Glu Val Thr Cys Val Val Leu Asp Leu Gly Arg Glu Asp Pro Glu
                20                  25                  30

Val Gln Ile Ser Trp Phe Val Asp Gly Lys Glu Val His Thr Ala Lys
            35                  40                  45

Thr Gln Ser Arg Glu Gln Gln Phe Asn Gly Thr Tyr Arg Val Val Ser
    50                  55                  60

Val Leu Pro Ile Glu His Gln Asp Trp Leu Thr Gly Lys Glu Phe Lys
65                  70                  75                  80

Cys Arg Val Asn His Ile Asp Leu Pro Ser Pro Ile Glu Arg Thr Ile
                85                  90                  95

Ser Lys Ala Arg Gly Arg Ala His Lys Pro Ser Val Tyr Val Leu Pro
            100                 105                 110

Pro Ser Pro Lys Glu Leu Ser Ser Ser Asp Thr Val Ser Ile Thr Cys
    115                 120                 125

Leu Ile Lys Asp Phe Tyr Pro Pro Asp Ile Asp Val Glu Trp Gln Ser
130                 135                 140

Asn Gly Gln Gln Glu Pro Glu Arg Lys His Arg Met Thr Pro Pro Gln
145                 150                 155                 160

Leu Asp Glu Asp Gly Ser Tyr Phe Leu Tyr Ser Lys Leu Ser Val Asp
                165                 170                 175

Lys Ser Arg Trp Gln Gln Gly Asp Pro Phe Thr Cys Ala Val Met His
            180                 185                 190

Glu Thr Leu Gln Asn His Tyr Thr Asp Leu Ser Leu Ser His Ser Pro
    195                 200                 205

Gly Lys
    210

<210> SEQ ID NO 4
<211> LENGTH: 196
<212> TYPE: PRT
<213> ORGANISM: Equus caballus
<220> FEATURE:
```

```
<221> NAME/KEY: misc_feature
<222> LOCATION: (1)...(196)
<223> OTHER INFORMATION: immunoglobulin IgG1 Fc region GenBank
      AAG01011.1

<400> SEQUENCE: 4
```

Phe Ile Phe Pro Pro Lys Pro Lys Asp Val Leu Lys Ile Ser Arg Lys
 1               5                  10                  15

Pro Glu Val Thr Cys Val Val Asp Leu Gly His Asp Asp Pro Asp
             20                  25                  30

Val Gln Phe Thr Trp Phe Val Asp Gly Val Glu Thr His Thr Ala Thr
             35                  40                  45

Thr Glu Pro Lys Glu Glu Gln Phe Asn Ser Thr Tyr Arg Val Val Ser
 50                  55                  60

Val Leu Pro Ile Gln His Gln Asp Trp Leu Phe Gly Lys Glu Phe Lys
 65                  70                  75                  80

Cys Ser Val Thr Ser Lys Ala Leu Pro Ala Pro Val Glu Arg Thr Thr
             85                  90                  95

Ser Lys Ala Lys Gly Gln Leu Arg Val Pro Gln Val Tyr Val Leu Ala
             100                 105                 110

Pro His Pro Asp Glu Leu Ala Lys Asn Thr Val Ser Val Thr Cys Leu
             115                 120                 125

Val Lys Asp Phe Tyr Pro Pro Glu Ile Asp Val Glu Trp Gln Ser Asn
 130                 135                 140

Glu His Pro Glu Pro Glu Gly Lys Tyr Ser Thr Thr Pro Ala Gln Leu
 145                 150                 155                 160

Asn Ser Asp Gly Ser Tyr Phe Leu Tyr Ser Lys Leu Ser Val Glu Thr
             165                 170                 175

Ser Arg Trp Lys Gln Gly Glu Ser Phe Thr Cys Gly Val Met His Glu
             180                 185                 190

Ala Leu His Asn
         195

```
<210> SEQ ID NO 5
<211> LENGTH: 209
<212> TYPE: PRT
<213> ORGANISM: Felis catus
<220> FEATURE:
<221> NAME/KEY: misc_feature
<222> LOCATION: (1)...(209)
<223> OTHER INFORMATION: immunoglobulin IgG1 Fc region GenBank
      AB016710.1

<400> SEQUENCE: 5
```

Phe Ile Phe Pro Pro Lys Pro Lys Asp Thr Leu Ser Ile Ser Arg Thr
 1               5                  10                  15

Pro Glu Val Thr Cys Leu Val Val Asp Leu Gly Pro Asp Asp Ser Asp
             20                  25                  30

Val Gln Ile Thr Trp Phe Val Asp Asn Thr Gln Val Tyr Thr Ala Lys
             35                  40                  45

Thr Ser Pro Arg Glu Glu Gln Phe Asn Ser Thr Tyr Arg Val Val Ser
 50                  55                  60

Val Leu Pro Ile Leu His Gln Asp Trp Leu Lys Gly Lys Glu Phe Lys
 65                  70                  75                  80

Cys Lys Val Asn Ser Lys Ser Leu Pro Ser Pro Ile Glu Arg Thr Ile
             85                  90                  95

Ser Lys Ala Lys Gly Gln Pro His Glu Pro Gln Val Tyr Val Leu Pro
             100                 105                 110

```
Pro Ala Gln Glu Glu Leu Ser Arg Asn Lys Val Ser Val Thr Cys Leu
        115                 120                 125
Ile Lys Ser Phe His Pro Pro Asp Ile Ala Val Glu Trp Glu Ile Thr
    130                 135                 140
Gly Gln Pro Glu Pro Glu Asn Asn Tyr Arg Thr Thr Pro Pro Gln Leu
145             150                 155                 160
Asp Ser Asp Gly Thr Tyr Phe Val Tyr Ser Lys Leu Ser Val Asp Arg
            165                 170                 175
Ser His Trp Gln Arg Gly Asn Thr Tyr Thr Cys Ser Val Ser His Glu
            180                 185                 190
Ala Leu His Ser His His Thr Gln Lys Ser Leu Thr Gln Ser Pro Gly
        195                 200                 205

Lys
```